(12) United States Patent
Högberg et al.

(10) Patent No.: US 8,901,356 B2
(45) Date of Patent: Dec. 2, 2014

(54) METHOD OF PRODUCING INGENOL-3-ANGELATE

(75) Inventors: Thomas Högberg, Åkarp (SE); Gunnar Grue-Sørensen, Roskilde (DK); Xifu Liang, Glostrup (DK); Anne Marie Horneman, Humlebaek (DK); Anders Klarskov Petersen, Naerum (DK)

(73) Assignee: Leo Laboratories Limited, Dublin (IE)

( * ) Notice: Subject to any disclaimer, the term of this patent is extended or adjusted under 35 U.S.C. 154(b) by 17 days.

(21) Appl. No.: 13/811,207

(22) PCT Filed: Jul. 8, 2011

(86) PCT No.: PCT/DK2011/000081
§ 371 (c)(1),
(2), (4) Date: Mar. 25, 2013

(87) PCT Pub. No.: WO2012/010172
PCT Pub. Date: Jan. 26, 2012

(65) Prior Publication Data
US 2013/0177952 A1 Jul. 11, 2013

Related U.S. Application Data

(60) Provisional application No. 61/366,018, filed on Jul. 20, 2010.

(51) Int. Cl.
| | |
|---|---|
| C07C 49/753 | (2006.01) |
| C07C 59/90 | (2006.01) |
| C07C 67/08 | (2006.01) |
| C07D 319/08 | (2006.01) |
| C07F 7/18 | (2006.01) |
| C07C 67/297 | (2006.01) |

(52) U.S. Cl.
CPC ........... *C07C 49/753* (2013.01); *C07C 2103/98* (2013.01); *C07C 67/08* (2013.01); *C07C 67/297* (2013.01); *C07D 319/08* (2013.01); *C07C 59/90* (2013.01); *C07F 7/184* (2013.01)
USPC ............ 568/369; 560/129; 556/436; 435/135

(58) Field of Classification Search
USPC ............ 568/369; 560/129; 556/436; 435/135
See application file for complete search history.

(56) References Cited

U.S. PATENT DOCUMENTS 7,449,492 B2 11/2008 Aylward et al.

OTHER PUBLICATIONS

International Search Report mailed Sep. 19, 2011, in corresponding PCT Patent Application No. PCT/DK2011/000081.
Hirota et al., "New Ingenol-Esters as Piscicidal Constituents of *Ephorbia cotinifolia* L.", Agric. Biol. Chem., 44 (6), 1351-1356 (1980).
Uemura et al, "Isolation and Structures of Irritant Substances Obtained from *Euphorbia* Species (Euphorbiaceae)", Tetrahedron Letters, No. 11, pp. 881-884 (1973).
Sorg et al., "Zur Chemie des Ingenols, 11[1] Ester des Ingenols und des $\Delta^{7,8}$-Isoingenols", Zietschrift Fur Naturforschung, vol. 37b, pp. 748-756 (1982).
Appendino et al, "Synthesis of Modified Ingenol Esters", European Journal of Organic Chemistry, pp. 3413-3420 (1999).
Kio et al., "Ingenol Esters From the Pro-Inflammatory Fraction of *Euphorbia kamerunica*", Phytochemistry, vol. 21, No. 3, pp. 725-726 (1982).
Baloch et al., "Bio-active compounds from *Euphorbia cornigera* Boiss", European Journal of Medicinal Chemistry, 44, 3188-3194 (2009).
Hohmann et al., "Diterpenoids from *Euphorbia peplus*", Planta Med., 66, 291-294 (2000).
Ogbourne et al., "Proceedings of the First International Conference on PEP005", Anti-Cancer Drugs, vol. 18, No. 3, pp. 357-362 (2007).
Bohlmann et al., "Struktur und Synthese eines aus *Bellis perennis* L. isolierten Diesters", Chem. Ber. 103, 561-563 (1970).
Hoskins et al., "Pyrrolizidine Alkaloid Analogues. Preparation of Semisynthetic Esters of Retronecine", J.C.S. Perkin I, pp. 538-544 (1977).
Beeby, Angeloyl Chloride: Synthesis and Utilisation in the Partial Synthesis of Lantadene A (Rehmannic Acid), Tetrahedron Letters, No. 38, pp. 3379-3382 (1977).
Opferkuch et al, "Zur Chemie des Ingenols I: Ingenol and einige seiner Derivate", Z. Naturforsch, 36b, 878-887 (1981).
Girin et al., "Determination of ingenol in homoeopathic mother tinctures of *Euphorbia* species by high-performance liquid chromatography", Journal of Chromatography, 637, 206-208 (1993).
Sayed et al., "Constituents of Egyptian Euphorbiaceae. IX. Irritant and cytotoxic ingenane esters from *Euphorbia paralias* L.", Experientia 36, 1206-1207 (1980).
Appendino et al., "An Expeditious Procedure for the Isolation of Ingenol from the Seeds of *Euphorbia lathyris*", J. Nat. Prod. 62, 76-79 (1999).

*Primary Examiner* — Sikarl Witherspoon
(74) *Attorney, Agent, or Firm* — Edwards Wildman Palmer LLP; Peter J. Manso

(57) ABSTRACT

The present invention relates to methods of producing ingenol-3-angelate (I) from ingenol (II).

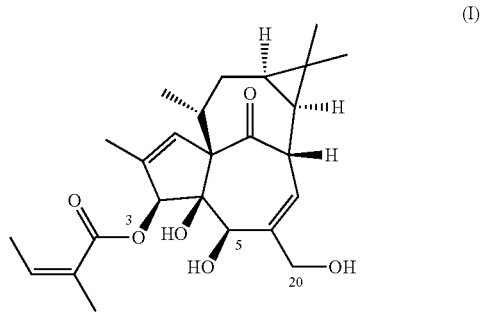

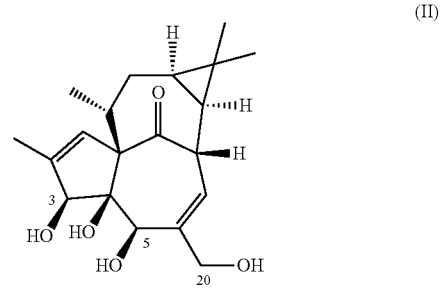

Furthermore, the invention relates to intermediates useful for the synthesis of ingenol-3-angelate (I) from ingenol (II) and to methods of producing said intermediates.

28 Claims, No Drawings

METHOD OF PRODUCING INGENOL-3-ANGELATE

CROSS-REFERENCE TO RELATED APPLICATIONS

This application is the U.S. national phase application pursuant to 35 U.S.C. §371 of PCT International Patent Application No. PCT/DK2011/000081, filed Jul. 8, 2011, which claims the benefit of and priority to U.S. Provisional Application No. 61/366,018, filed Jul. 20, 2010. The entire contents of the aforementioned patent application are incorporated herein by this reference.

FIELD OF THE INVENTION

The present invention relates to methods of producing ingenol-3-angelate (2-methyl-2(Z)-butenoic acid (1aR,2S, 5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester; PEP005, ingenol mebutate) from ingenol. The present invention further provides novel intermediates and methods for the synthesis of the intermediates useful for producing ingenol-3-angelate.

BACKGROUND OF THE INVENTION

Ingenol-3-angelate (PEP005, ingenol mebutate) is a protein kinase C activator in phase III clinical development for the treatment of actinic keratosis. The drug candidate is also in phase II trials for non-melanoma skin cancer [Ogbourne, S. M.; *Anti-cancer Drugs*, (2007), 18, 357-62].

The compound ingenol-3-angelate (PEP005) [Sayed, M. D. et. al.; *Experienta*, (1980), 36, 1206-1207] can be isolated from various *Euphorbia* species, and particularly from *Euphorbia peplus* [Hohmann, J. et. al; *Planta Med.*, (2000), 66, 291-294] and *Euphorbia drummondii* by extraction followed by chromatography as described in U.S. Pat. No. 7,449,492. According to this procedure, extraction of 17 kg of fresh *Euphorbia peplus* affords 7 g of a crude oil, which subsequently must be purified by HPLC to afford pure ingenol-3-angelate. The purification method is not ideally suited for larger scale production, as chlorophyll, which otherwise would co-migrate with ingenol-3-angelate, must be removed from the extract before the final purification step. Thus, the yield of ingenol-3-angelate by extraction from *Euphorbia peplus* and subsequent chromatography is extremely low. Therefore an alternative process for the production of ingenol-3-angelate which is also suitable for larger scale production would be desirable.

Ingenol is a natural product which is easily extracted from the readily available seeds of *Euphorbia lathyris* [Appendino, G. et. al., *J. Nat. Prod.* (1999), 62, 76-79]. As part of the extraction procedure the various ingenol esters present are hydrolysed and thus the amount of isolated ingenol is increased, making ingenol more readily available than ingenol-3-angelate [Appendino, G. et. al., *J. Nat. Prod.* (1999), 62, 76-79; Girin, M. A. et. al., *J. Chromatogr.*, (1993), 637, 206-208].

Ingenol or ingenol esters may also be found in other *Euphorbia* species, for example ingenol or ingenol esters have also been found in *E. acrurensis, E. antiquorum, E. biglandulosa, E. canariensis, E. cooperi, E. cotinifolia, E. deightonii, E. desmondi, E. drupifera, E. ebracteolata, E. esula, E. helioscopia, E. hermentiana, E. iberica, E. ingens, E. jolkini, E. kamerunica, E. kansui, E. leuconeura, E. matabelensis, E. megalantha, E. millii, E. myrsinites, E. nematocypha, E. nubica, E. palustris, E. peplus, E. petiolata, E. pilosa, E. quadrialata, E. quinquecostata, E. resinifera, E. royleana, E. seguieriana, E. serrata, E. sieboldiana, E. tirucalli, E. triangularis, E. trigona*. Furthermore, ingenol is commercially available, for example from LC Laboratories, 165 New Boston Street, Woburn, Mass. 01801, USA.

Ingenol has previously been used as a starting point for the semi-synthetic preparation of ingenol-3-esters [Sorg, B. et. al, *Z. Naturforsch.*, (1982), 37B, 748-756] and ingenol-3-ester derivatives [Appendino et. al., *Eur. J. Org. Chem.* (1999), 3413; Opferkuch et. al., *Z. Naturforschung*, (1981), 36B, 878]. However, the preparation of ingenol-3-angelate and ingenol-3-angelate derivatives from ingenol has not been described. The preparation of angelate esters is not straightforward as angelic acid and angelate esters are prone to isomerisation of the double bond to form the tiglate ester, both with and without the presence of base [Beeby, P., *Tetrahedron Lett.* (1977), 38, 3379-3382, Hoskins, W. M., *J. Chem. Soc. Perkin Trans.* 1, (1977), 538-544, Bohlmann, F. et. al., *Chem. Ber.* (1970), 103, 561-563]. Furthermore, ingenol derivatives are known to degrade in the presence of acid [Appendino et. al., *Eur. J. Org. Chem.* (1999), 3413]. Also, ingenol-3-esters are readily rearranged to afford the ingenol-5-esters and ingenol-20-esters. This is particularly the case for esters of short-chain carboxylic acids [Sorg, B. et. al, *Z. Naturforsch.*, (1982), 37B, 748-756]. The purification method previously described for the purification of ingenol-3-esters to avoid the rearranged side-products [Sorg, B. et. al, *Z. Naturforsch.*, (1982), 37B, 748-756] is not suitable for large scale production of ingenol-3-angelate.

SUMMARY OF THE INVENTION

It is an object of this invention to provide a scalable process for the synthesis of ingenol-3-angelate (PEP005) starting from ingenol.

The present invention provides novel processes to produce ingenol-3-angelate from ingenol. The present invention further provides novel intermediates for the preparation of ingenol-3-angelate.

Thus, in one aspect, the invention relates to methods of producing ingenol-3-angelate (I) from ingenol (II).

In another aspect, the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

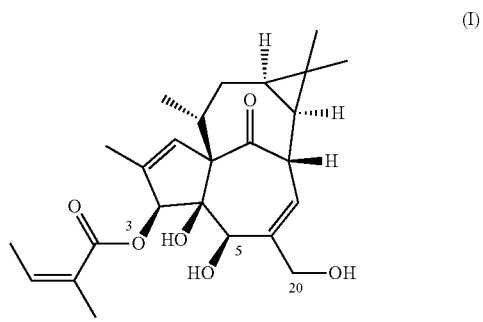

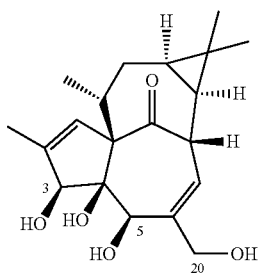

(II)

comprising the steps of:

(a) reacting one or both hydroxyl groups in positions 5 and 20 of ingenol with suitable hydroxyl protecting agents, same or different, to obtain a compound of the general formula (III) or (IV), i.e. protecting one or both hydroxyl groups in positions 5 and 20 of ingenol with a protective group to obtain a compound of the general formula (III) or (IV)

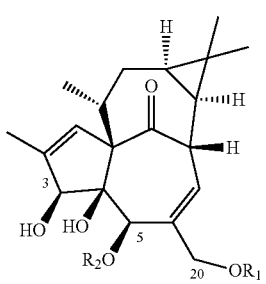

(III)

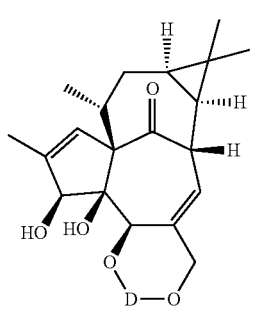

(IV)

wherein $R_1$ represents hydrogen or a hydroxyl protective group and $R_2$ represents hydrogen or a hydroxyl protective group, or $R_1$ represents a hydroxyl protective group and $R_2$ represents hydrogen or a hydroxyl protective group, or wherein D represents a dihydroxyl protective group (b) esterifying compounds (III) or (IV) to obtain compounds of the general formula (V) or (VI), i.e. esterifying the hydroxyl group at the 3-position of compounds (III) or (IV) to obtain compounds of the general formula (V) or (VI)

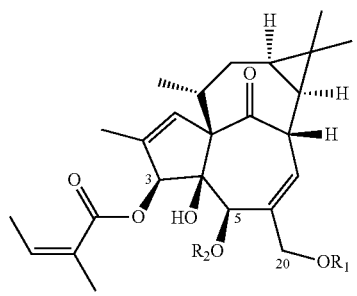

(V)

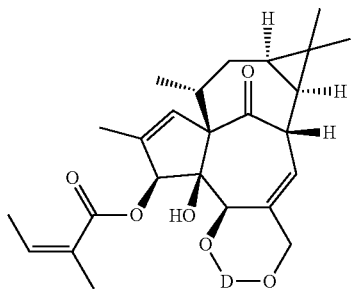

(VI)

wherein $R_1$, $R_2$ and D are as described above, and (c) removing the hydroxyl protective groups $R_1$, or $R_1$ and $R_2$, or D from compounds (V) or (VI) to obtain ingenol-3-angelate (I).

In another aspect, the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

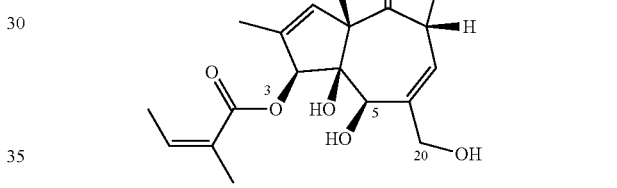

(I)

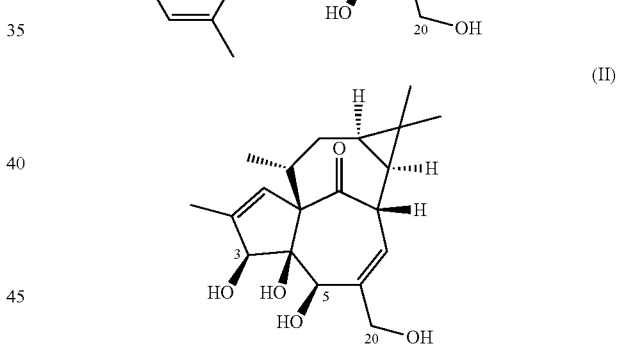

(II)

comprising the steps of:

(d) esterifying ingenol (II) to obtain a compound of the formula (VII)

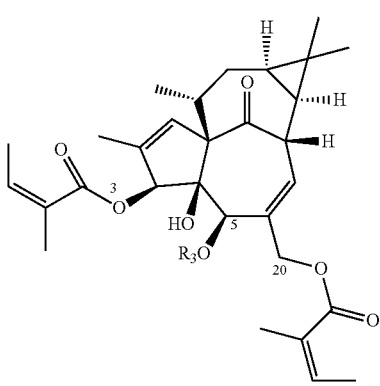

(VII)

wherein R₃ represents hydrogen or angeloyl, i.e. esterifying the 3- and the 20-hydroxyl group and optionally esterifying the 5-hydroxyl group of ingenol (II) to obtain a compound of the formula (VII) and (e) cleaving the angelate ester(s) in position 20 or in position 5 and 20 of compound (VII) to obtain ingenol-3-angelate (I).

In a further aspect, the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

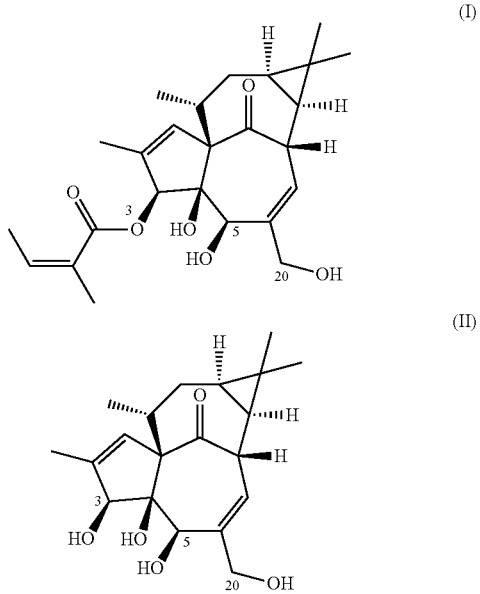

comprising the step of:
(f) selective esterification of the 3-hydroxy group of compound (II) to obtain ingenol-3-angelate (I).

In another aspect, the invention relates to a compound of general structure (V) wherein R₁ represents hydrogen or a hydroxyl protective group and R₂ represents hydrogen or a hydroxyl protective group;
with the proviso that not both R₁ and R₂ represent hydrogen:
and with the proviso that R₁ and R₂ do not represent acetyl;
and with the proviso that R₁ and R₂ do not represent 2-[(2-aminobenzoyl)amino]benzoyl;
and with the proviso that R₁ does not represent decanoyl;
and with the proviso that R₁ does not represent 3-phenyl-2-propenoyl.

In another aspect the invention relates to a compound of general structure (VI) wherein D represents a dihydroxyl protective group; with the proviso that D does not represent isopropylidene.

In another aspect, the invention relates to a compound of general formula III wherein R₁ and R₂ independently represents hydrogen or an ether, acetal, ketal, silylether, or a sulfenate derived hydroxyl protective group;
with the proviso that not both R₁ and R₂ represent hydrogen;
and with the proviso that R₁ does not represent triphenylmethyl;
and with the proviso that R₁ does not represent t-butyldimethylsilyl.

In another aspect, the invention relates to a compound of general formula IV wherein D represents a dihydroxyl protective group;
with the proviso that D does not represent isopropylidene.

DETAILED DESCRIPTION OF THE INVENTION

Definitions

All terms are intended to be understood as they would be understood by a person skilled in the art.

The term "hydroxyl protecting agent" is intended to mean a reagent which under suitable reaction conditions reacts with a hydroxyl group to form a hydroxyl protective group.

The term "hydroxyl protective group" is intended to include any group which forms a derivative of the hydroxyl group that is stable to the projected reactions wherein said hydroxyl protective group subsequently optionally can be selectively removed. Said hydroxyl derivative can be obtained by selective reaction of a hydroxyl protecting agent with a hydroxyl group.

The term "hydroxyl protecting group" is intended to have the same meaning as the term "hydroxyl protective group".

Ether derivatives, such as allyl ether, prenyl ether, p-methoxybenzyl ether, triphenylmethyl ether, 2-trimethylsilylethyl ether, tert-butyl ether, cinnamyl ether, propargyl ether, p-methoxyphenyl ether, benzyl ether, 3,4-dimethoxybenzyl ether, 2,6-dimethoxybenzyl ether, o-nitrobenzyl ether, p-nitrobenzyl ether, 4-(trimethylsilylmethyl)-benzyl ether, 2-naphthylmethyl ether, diphenylmethyl ether, (4-methoxyphenyl)-phenylmethyl ether, (4-phenyl-phenyl)-phenylmethyl ether, p,p'-dinitrobenzhydryl ether, 5-dibenzosuberyl ether, tris(4-tert-butylphenyl)methyl ether, (α-naphthyl)-diphenylmethyl ether, p-methoxyphenyldiphenylmethyl ether, di(p-methoxyphenyl)phenylmethyl ether, tri(p-methoxyphenyl)methyl ether or 9-(9-phenyl)xanthenyl ether are examples of hydroxyl protecting groups.

Ether derived hydroxyl protective groups also include alkoxyalkylethers (acetals and ketals) such as 1-ethoxyethyl ether, 1-methyl-1-methoxyethyl ether, [(3,4-dimethoxybenzyl)oxy]methyl ether, guaiacolmethyl ether, 2-methoxyethoxymethyl ether, 2-(trimethylsilyl)ethoxymethyl ether, tetrahydropyranyl ether, tetrahydrofuranyl ether, methoxymethyl ether benzyloxymethyl ether, p-methoxybenzyloxymethyl ether, p-nitrobenzyloxymethyl ether, o-nitrobenzyloxymethyl ether, (4-methoxyphenoxy)methyl ether, tert-butoxymethyl ether, 4-pentenyloxymethyl ether, siloxymethyl ether, 1-methoxycyclohexyl ether, 4-methoxytetrahydropyranyl ether, 1-[(2-chloro-4-methyl)phenyl]-4-methoxypiperidin-4-yl ether, 1-(2-fluorophenyl)-4-methoxypiperidin-4-yl ether, 1-(4-chlorophenyl)-4-methoxypiperidin-4-yl ether or 1-methyl-1-benzyloxyethyl ether.

Ether derived hydroxyl protective groups also include thioacetals and thio ketals such as tetrahydrothiopyranyl ether, 4-methoxytetrahydrothiopyranyl ether, tetrahydrothiofuranyl ether or 1,3-benzodithiolan-2-yl ether.

Hydroxyl protective groups also include silyl ether derivatives, such as trimethylsilyl ether, triethylsilyl ether, triisopropylsilyl ether, tert-butyldimethylsilyl ether, dimethylisopropylsilyl ether, diethylisopropylsilyl ether, diphenylmethylsilyl ether, triphenylsilyl ether, dimethylthexylsilyl ether, 2-norbornyldimethylsilyl ether, tert-butyldiphenylsilyl ether, (2-hydroxystyryl)dimethylsilyl ether, (2-hydroxystyryl)diisopropylsilyl ether, tert-butylmethoxyphenylsilyl ether or tert-butoxydiphenylsilyl ether.

Hydroxyl protective groups also include esters of hydroxyl groups such as acetate ester, chloroacetate ester, trifluoroacetate ester, phenoxyacetate ester, formate ester, benzoylformate ester, dichloroacetate ester, trichloroacetate ester, methoxyacetate ester, p-chlorophenoxyacetate ester, phenylacetate ester, 3-phenylpropionate ester, 4-pentenoate ester, 4-oxopentanoate ester, pivaloate ester, crotonate ester, 4-methoxycrotonate ester, angelate ester, benzoate ester or p-phenylbenzoate ester.

Hydroxyl protective groups also include carbonates of hydroxyl groups such as methoxymethyl carbonate, 9-fluorenylmethyl carbonate, methyl carbonate, ethyl carbonate, 2,2,2-trichloroethyl carbonate, 2-(trimethylsilyl)ethyl carbonate, vinyl carbonate, allyl carbonate or p-nitrophenyl carbonate.

Hydroxyl protective groups also include sulfenates of hydroxyl groups such as 2,4-dinitrophenylsulfenate.

A dihydroxyl protective group is any group which forms a derivative of a diol which is stable to the projected reactions wherein said dihydroxyl protective group subsequently optionally can be selectively removed. Said dihydroxyl derivative can be obtained by selective reaction of a dihydroxyl protecting agent with a diol.

Ketal derivatives, such as isopropylidene ketal (acetonide), cyclopentylidene ketal, cyclohexylidene ketal, cycloheptylidene ketal, benzophenone ketal, 1-tert-butylethylidene ketal or 1-phenylethylidene ketal, 3-pentylidene ketal, 2,4-dimethyl-3-pentylidene ketal, 2,6-dimethyl-4-heptylidene ketal, 3,3-dimethyl-2-butylidene ketal; and acetal derivatives such as benzylidene acetal, 2,4-dimethoxybenzylidene acetal, 4-nitrobenzylidene acetal, 2,4,6-trimethylbenzylidene acetal, 2,2-dimethyl-1-propylidene acetal, methylene acetal, ethylidene acetal, p-methoxybenzylidene acetal, tert-butylmethylidene acetal, 3-(benzyloxy)propylidene acetal, acrolein acetal, 2-nitrobenzylidene acetal, mesitylene acetal or 2-naphthaldehyde acetal, are examples of dihydroxyl protective groups.

Other dihydroxyl protective groups include cyclic ortho esters or ortho esters, such as methoxymethylene acetal, ethoxymethylene acetal, 2-oxacyclopentylidene ortho ester or isopropoxymethylene acetal.

Other dihydroxyl protective groups include bisacetal derivatives such as butane 2,3-bisacetal or cyclohexane-1,2-diacetal; or dispiroketals such as octahydro-[2,2']-bipyranyl ketal.

Other dihydroxyl protective groups include silyl derivatives such as di-tert-butylsilylene, dialkylsilylene, 1,3-(1,1,3,3-tetraisopropyldisiloxanylidene), 1,1,3,3-tetra-tert-butoxydisiloxanylidene, methylene-bis-(diisopropylsilanoxanylidene, or 1,1,4,4-tetraphenyl-1,4-disilanylidene derivatives.

Dihydroxyl protective groups also include cyclic carbonates.

Other dihydroxyl protective groups include cyclic boronates such as phenyl boronate, methyl boronate or ethyl boronate.

Hydroxyl protective groups and dihydroxyl protective groups also include solid phase supported protective groups. Solid phase supported reagents for the introduction of solid phase supported protective groups may include for example polymer-bound 2-Chlorotrityl chloride for the introduction of a solid phase supported trityl protective group, or Acetylpolystyrene resin or 4-(4-Hydroxyphenyl)butan-2-one-based resins for the preparation of solid phase supported ketal-protective groups.

Non-limiting examples of hydroxyl protective groups and dihydroxyl protective groups all included in the scope of this invention, can for example be found in "Protective Groups in Organic Synthesis", 4$^{th}$ ed. P. G. M. Wuts; T. W. Greene, John Wiley, 2007, page 16-366, and in P. J. Kocienski, "Protecting Groups", 3$^{rd}$ ed. G. Thieme, 2003, which are hereby incorporated by reference Angelic acid is 2-methyl-2(Z)-butenoic acid.

Tiglic acid is 2-methyl-2(E)-butenoic acid.

The term "alkyl" is intended to indicate a radical obtained when one hydrogen atom is removed from a hydrocarbon. Said alkyl comprises 1-20, preferably 1-12, such as 1-6 carbon atoms. The term includes the subclasses normal alkyl (n-alkyl), secondary and tertiary alkyl, such as methyl, ethyl, n-propyl, isopropyl, n-butyl, isobutyl, sec-butyl, tert-butyl, pentyl and isopentyl.

The term "alkenyl" is intended to indicate a radical obtained when one hydrogen atom is removed from a hydrocarbon containing at least one C=C double bond. Said alkenyl comprises 3-12, preferably 3-6 carbon atoms, e.g. allyl.

The term alkyl halide is intended to indicate a molecule of the general formula R—X, wherein R is an optionally substituted alkyl group as defined above, and X is any halogen substituent such as chloro, bromo or iodo.

The term alkenyl halide is intended to indicate a molecule of the general formula R—X, wherein R is an optionally substituted alkenyl group as defined above, and X is any halogen substituent such as chloro, bromo or iodo. The term "alkoxy" is intended to indicate a radical of the formula —OR', wherein R' is alkyl as indicated above, e.g. methoxy, ethoxy, n-propoxy, isopropoxy, butoxy, etc.

The term "alkoxyalkyl" is intended to indicate an alkyl radical as defined above, which is substituted with an alkoxy radical as defined above, i.e. R'—O—R'—, wherein each R' is alkyl same or different, as indicated above, e.g. methoxymethyl, ethoxymethyl.

The term "alkoxyalkyl halide" is intended to indicate a molecule of the general formula R'—O—R'—X wherein each R' is alkyl, same or different, as indicated above, and X is any halogen substituent such as chloro, bromo or iodo, e.g. methoxymethyl chloride, ethoxymethyl chloride.

The term "alkylcarbonyl" is intended to indicate a radical of the formula —C(O)—R', wherein R' is alkyl as indicated above, e.g. acetyl.

The term "alkenylcarbonyl" is intended to indicate a radical of the formula —C(O)—R', wherein R' is alkenyl as indicated above, e.g. angeloyl.

The term "aryl" is intended to indicate a radical of the formula Ar—, obtained when one hydrogen atom is removed from a cyclic carbon containing compound with a delocalised (4n+2) π-electron system. n is an integer >0, preferably 1 or 2. Examples of Ar— are phenyl, 2,4,6-trichlorophenyl, 4-nitrophenyl.

The term "arylalkyl" is intended to indicate a radical of the formula Ar—R''—, wherein Ar—R''— is an alkyl radical as indicated above substituted with an aromatic radical, e.g. benzyl.

The term "acid halide" is intended to indicate a molecule of the general formula R'—C(O)—X or Ar—C(O)—X wherein R' is optionally substituted alkyl or alkenyl as defined above, Ar is optionally substituted aryl as defined above and X is halogen such as chloro, bromo or iodo, as defined herein. Examples of acid halides are acetyl chloride, chloroacetyl chloride, phenoxyacetyl chloride, benzoyl chloride, 2,4,6-trichlorobenzoyl chloride, 4-nitrobenzoyl chloride or angeloyl chloride.

The term "acid anhydride" is intended to indicate a molecule of the general formula R'—C(O)—O—C(O)—R' or Ar—C(O)—O—C(O)—Ar wherein R' is optionally substituted alkyl or alkenyl as defined above and Ar is optionally substituted aryl as defined above. Examples of acid anhydrides are acetic anhydride, angelic anhydride, benzoic anhydride or 2,4,6-trichlorobenzoic anhydride.

The term "mixed anhydride" is intended to indicate a molecule of the general formula R—C(O)—O—C(O)—R" or Ar—C(O)—O—C(O)—R' wherein R— and R'— are different and R' and R" are optionally substituted alkyl or alkenyl as defined above and Ar is optionally substituted aryl as defined above. Examples of "mixed anhydrides" are angeloyl 2,4,6-trichlorobenzoyl anhydride or angeloyl 4-nitrobenzoyl anhydride.

The term "alkoxycarbonyl" is intended to indicate a radical of the formula R'—O—C(O)—, wherein R' is alkyl as indicated above, e.g. methoxycarbonyl, ethoxycarbonyl, n-propoxycarbonyl, isopropoxycarbonyl, tert-butoxycarbonyl etc.

The term "arylsulfenyl" is intended to indicate a radical of the formula Ar—S(O)— wherein Ar— is as defined above, e.g. 2,4-dinitrophenylsulfenyl.

The term "diol" is intended to indicate a molecule containing two or more hydroxyl groups, in which the two hydroxyl groups are not attached to the same carbon atom. In general diol protecting groups are used for protection of 1,2-diols and/or 1,3-diols. Examples of "diols" are ingenol or ingenol-3-angelate.

The term "activated acid derivative" is intended to indicate a derivative of an acid, which under the chosen reaction conditions will react more readily than the corresponding acid with an alcohol to form an ester. Examples of "activated acid derivatives" are acid halides, acid anhydrides, "mixed anhydrides", methyl angelate or vinyl angelate.

The term "coupling reagent" is intended to indicate a reagent, which will facilitate the formation of an ester from an acid and an alcohol by the formal binding of water. Examples of "coupling reagents" are dicyclohexylcarbodiimide (DCC), 1-methyl-2-chloro-pyridinium iodide, HBTU (O-(benzotriazol-1-yl)-N,N,N',N'-tetramethyluronium hexafluorophosphate), DMTMM (4-(4,6-dimethoxy-1,3,5-triazin-2-yl)-4-methylmorpholinium chloride), HATU (N,N,N',N'-Tetramethyl-O-(7-azabenzotriazol-1-yl)uronium hexafluorophosphate), EDCI (N-(3-Dimethylaminopropyl)-N'-ethylcarbodiimide hydrochloride).

The term "activator" is intended to indicate a reagent, which will facilitate the formation of an ester from an acid or an activated acid derivative and an alcohol by the removal of acid from the reaction mixture. Examples of "activators" are triethylamine, N,N-diisopropylethylamine, pyridine or lutidine.

The term "catalyst" is intended to indicate a compound, which in substoichiometric or stoichiometric amount, or in excess, will accelerate the reaction without being consumed itself. Examples of a catalyst is DMAP (4-(N,N-dimethylamino)pyridine) or 1-hydroxybenzotriazole.

The term "enzymatic catalysis" is intended to indicate catalysis of chemical reactions by specialised proteins called enzymes. Examples of enzymes are lipases, esterases, proteases or cutinases.

The term "esterase" is intended to indicate an enzyme which is capable of catalysing the cleavage of an ester into acid and alcohol.

The term "lipase" is intended to indicate an enzyme which is capable of catalysing the hydrolysis of lipids. Lipases are often capable of hydrolysing esters that are not lipids. An example of a lipase is *Candida antarctica* Lipase B.

The term "angelate" is intended to indicate an ester of angelic acid.

The term "esterify" is intended to indicate a reaction in which a hydroxyl group is combined with a suitable reactant, i.e. combined with a carboxylic acid or a carboxylic acid derivative under suitable reaction conditions, to form an ester.

The term "ether derived hydroxyl protective group" is intended to indicate a hydroxyl protecting group in which the hydroxyl group to be protected is part of an ether group.

The term "ester derived hydroxyl protective group" is intended to indicate a hydroxyl protecting group in which the hydroxyl group to be protected is part of an ester group.

The term "acetal derived hydroxyl protective group" is intended to indicate a hydroxyl protecting group in which the hydroxyl group to be protected is part of an acetal group.

The term "ketal derived hydroxyl protective group" is intended to indicate a hydroxyl protecting group in which the hydroxyl group to be protected is part of a ketal group.

The term "silylether derived hydroxyl protective group" is intended to indicate a hydroxyl protecting group in which the hydroxyl group to be protected is part of a silylether group.

The term "sulfenate derived hydroxyl protective group" is intended to indicate a hydroxyl protecting group in which the hydroxyl group to be protected is part of a sulfenate group.

The term "boronate derived hydroxyl protective group" is intended to indicate a hydroxyl protecting group in which the hydroxyl group to be protected is part of a boronate group.

The term "carbonate derived hydroxyl protective group" is intended to indicate a hydroxyl protecting group in which the hydroxyl group to be protected is part of a carbonate group.

Embodiments

In one embodiment, the invention relates to methods of producing ingenol-3-angelate (I) from ingenol (II), in which one or more hydroxyl groups are protected by hydroxyl protective groups or dihydroxyl protective groups.

In one embodiment the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

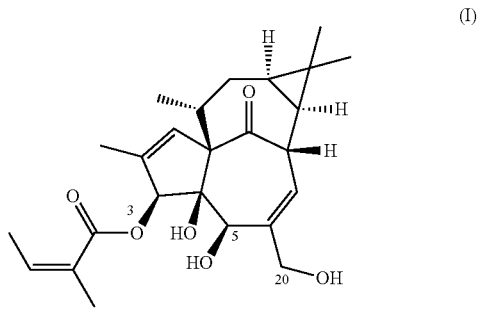

comprising the steps of:

(a) protecting one or both hydroxyl groups in positions 5 and 20 of ingenol with a protective group to obtain a compound of the general formula (III) or (IV)

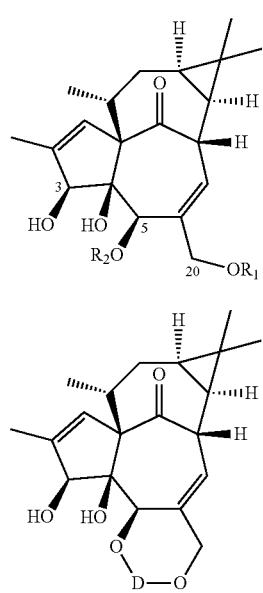

wherein $R_1$ represents a hydroxyl protective group and $R_2$ represents hydrogen or a hydroxyl protective group, or wherein D represents a dihydroxyl protective group (b) esterifying compounds (III) or (IV) to obtain compounds of the general formula (V) or (VI)

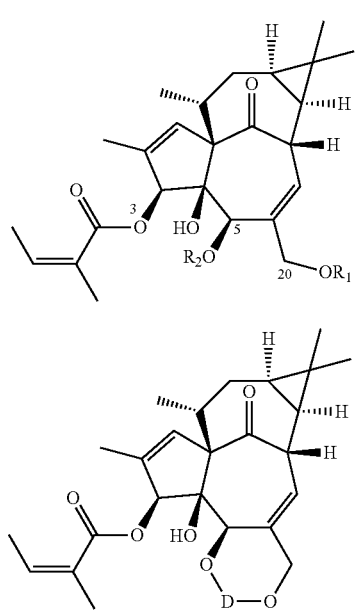

wherein $R_1$, $R_2$ and D are as described above, and (c) removing the hydroxyl protective groups $R_1$, or $R_1$ and $R_2$, or D from compounds (V) or (VI) to obtain ingenol-3-angelate (I).

In another embodiment the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

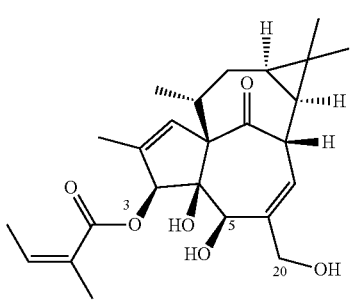

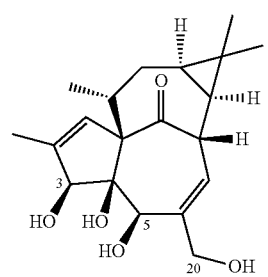

comprising the steps of:

(d) esterifying ingenol (II) to obtain a compound of the formula (VII)

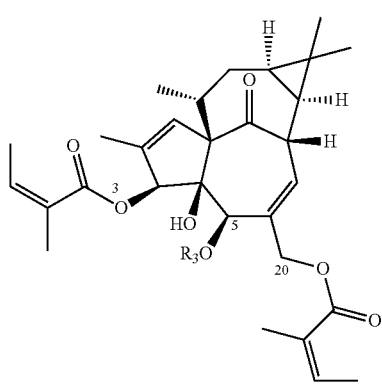

wherein $R_3$ represents hydrogen or angeloyl, and (e) cleaving the angelate ester(s) in position 20 or in position 5 and 20 of compound (VII) to obtain ingenol-3-angelate (I).

In another embodiment the invention relates to a method of producing ingenol-3-angelate (2-Methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester) (I) from ingenol (II)

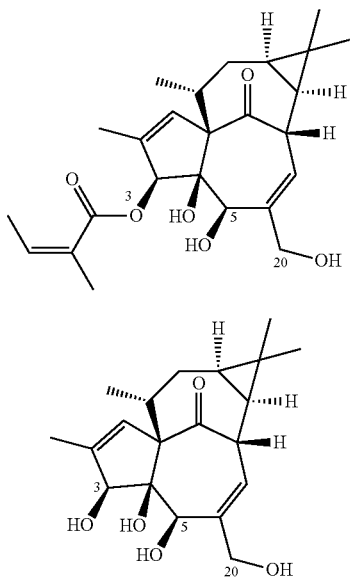

comprising the step of:
(f) selective esterification of the 3-hydroxy group of compound (II) to obtain ingenol-3-angelate (I).

In one embodiment, $R_1$ may represent hydrogen or $R_1$ may represent an ether, acetal, ketal, silylether, ester, carbonate, or a sulfenate derived hydroxyl protective group and $R_2$ may represent hydrogen or an ether, acetal, ketal, silylether, ester, carbonate, or a sulfenate derived hydroxyl protective group.

For example, $R_1$ may be selected from the group consisting of hydrogen, [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, acetyl, chloroacetyl, phenoxyacetyl or angeloyl.

$R_2$ may for instance be selected from the group consisting of hydrogen or [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, acetyl, chloroacetyl, phenoxyacetyl or angeloyl.

In another embodiment, D may represent an acetal, ketal, diacetal, diketal, ortho ester, silyl, boronate or a carbonate derived dihydroxyl protective group. For example, D may be selected from the group consisting of isopropylidene, cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene,benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

In a specific embodiment, $R_1$ represents a hydroxyl protective group, and $R_2$ represents hydrogen.

In another specific embodiment, $R_3$ represents hydrogen.

In another embodiment the invention relates to a method wherein step (b) comprises reacting compound (III) or (IV), wherein $R_1$, $R_2$ and D are as defined above with angelic acid in the presence of a coupling reagent or an enzyme.

In another embodiment the invention relates to a method wherein step (b) comprises reacting compound (III) or (IV), wherein $R_1$, $R_2$ and D are as defined above with angelic acid in the presence of a coupling reagent.

In an embodiment the coupling reagent is selected from the group consisting of DCC, HATU, EDCI or 2-chloro-1-methyl-pyridinium iodide In another embodiment the invention relates to a method wherein step (b) comprises reacting compound (III) or (IV), wherein $R_1$, $R_2$ and D are as defined above, with an activated derivative of angelic acid.

In an embodiment the activated derivative of angelic acid is selected from the group consisting of methyl angelate, angeloyl chloride, angelic acid anhydride, [(Z)-2-methylbut-2-enoyl]2,4,6-trichlorobenzoate or angeloyl 4-nitrobenzoyl anhydride.

In another embodiment the invention relates to a method wherein step (b) comprises reacting compound (III) or (IV), wherein $R_1$, $R_2$ and D are as defined above, with an angelic acid halide or with angelic acid anhydride or with a mixed angelic acid anhydride.

In an embodiment angelic acid halide is angeloyl chloride.
In an embodiment a mixed angelic anhydride is [(Z)-2-methylbut-2-enoyl]2,4,6-trichlorobenzoate or angeloyl 4-nitrobenzoyl anhydride.

In an embodiment the invention relates to a compound of general formula (V) wherein $R_1$ represents hydrogen or an ether, acetal, ketal, silylether, ester, carbonate, or a sulfenate derived hydroxyl protective group, and $R_2$ represents hydrogen or an ether, acetal, ketal, silylether, ester, carbonate, or a sulfenate derived hydroxyl protective group;

In an embodiment the invention relates to a compound of general formula (V) wherein $R_1$ and $R_2$ independently represents hydrogen or [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, chloroacetyl or phenoxyacetyl.

In an embodiment the invention relates to a compound of general formula (V) wherein $R_1$ represents a hydroxyl protective group and $R_2$ represents hydrogen;

In an embodiment the invention relates to a compound chosen from the group consisting of
Ingenol-20-(tert-butyldimethylsilyl)-ether-3-angelate.

In an embodiment the invention relates to a compound of general formula (VI) wherein D represents an acetal, ketal, diacetal, diketal, ortho ester, silyl, boronate or a carbonate dihydroxyl protective group.

In an embodiment the invention relates to a compound of general formula (VI) wherein D represents cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene, benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

In an embodiment the invention relates to a compound chosen from the group consisting of
ingenol-5,20-(di(tert-butyl)silylene)-ether-3-angelate In an embodiment the invention relates to a compound of general formula (IV) wherein D represents an acetal, ketal, diacetal, diketal, ortho ester, silyl, boronate or a carbonate derived dihydroxyl protective group.

In an embodiment the invention relates to a compound of general formula (IV) wherein D represents cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene, benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

In an embodiment the invention relates to a compound chosen from the group consisting of
Ingenol-5,20-(3-pentylidene)-ketal,
Ingenol-5,20-(2,4-dimethyl-3-pentylidene)-ketal,
Ingenol-5,20-(2,6-dimethyl-4-heptylidene)-ketal,
Ingenol-5,20-cyclopentylidene-ketal,
Ingenol-5,20-cyclohexylidene-ketal,
Ingenol-5,20-(3,3-dimethyl-2-butylidene)-ketal,
Ingenol-5,20-(1-phenyl-1-ethylidene)-ketal,
Ingenol-5,20-benzylidene-acetal,
Ingenol-5,20-(4-methoxybenzylidene)-acetal,
Ingenol-5,20-(2,4-dimethoxybenzylidene)-acetal,
Ingenol-5,20-(4-nitrobenzylidene)-acetal,
Ingenol-5,20-(2,4,6-trimethylbenzylidene)-acetal,
Ingenol-5,20-(2,2-dimethyl-1-propylidene)-acetal,
Ingenol-5,20-methyl-orthoformate,
Ingenol-5,20-ethyl-orthoformate,
Ingenol-5,20-(prop-2-yl)-orthoformate, or
Ingenol-5,20-(di(tert-butyl)silylene)-ether.

In an embodiment the invention relates to a compound a compound of general structure (VII) wherein $R_3$ represents hydrogen or angeloyl.

In an embodiment the invention relates to the use of a compound of general formula (III), (IV), (V) or (VI) as an intermediate in the manufacture of ingenol-3-angelate.

Synthetic Methods

The compounds of the general formula (III) and (IV) can for example be synthesised by reacting compound (II) with a hydroxyl protecting agent or a dihydroxyl protecting agent according to methods well known to a person skilled in the art, such as methods described in "Protective Groups in Organic Synthesis", $4^{th}$ ed. P. G. M. Wuts; T. W. Greene, John Wiley, 2007 or in P. J. Kocienski, "Protecting Groups", $3^{rd}$ ed. G. Thieme, 2003 and references cited therein.

For example, compound (III) wherein $R_1$ is triphenylmethyl and $R_2$ is hydrogen or triphenylmethyl, can be synthesised by reacting compound (II) with a triphenylmethyl reagent such as triphenylmethylpyridinium fluoroborate or triphenylmethyl chloride in a suitable solvent such as pyridine, N,N-dimethylformamide or dichloromethane in the presence or in the absence of base [eg. Opferkuch et. al., *Z. Naturforschung*, (1981), 36B, 878].

Compound (III) wherein $R_1$ is arylalkyl or alkenyl such as p-methoxybenzyl or allyl and $R_2$ is hydrogen or arylalkyl or alkenyl, can for example be synthesised by reacting compound (II) with an alkyl halide or alkenyl halide such as p-methoxybenzyl halide or allyl halide in a suitable solvent such as N,N-dimethylformamide or tetrahydrofuran optionally in the presence of a suitable base such as potassium carbonate.

Compound (III) wherein $R_1$ is alkoxyalkyl such as methoxymethyl or 2-methoxyethoxymethyl and $R_2$ is hydrogen or alkoxyalkyl such as methoxymethyl or 2-methoxyethoxymethyl, can for example be synthesised by reacting compound (II) with an alkoxyalkyl halide such as methoxymethyl chloride or 2-methoxyethoxymethyl chloride in a suitable solvent such as tetrahydrofuran or dichloromethane optionally in the presence of a suitable base such as N,N-diisopropylethylamine.

Compound (III) wherein $R_1$ is 2-tetrahydropyranyl and $R_2$ is hydrogen or 2-tetrahydropyranyl, can for example be synthesised by reacting compound (II) with dihydropyran in a suitable solvent such as dichloromethane or acetonitrile in the presence of a suitable acid such as p-toluenesulfonic acid.

Compound (III) wherein $R_1$ is silyl and $R_2$ is hydrogen or silyl, can for example be synthesised by reacting compound (II) with a silyl chloride such as tert-butyldimethylsilyl chloride, tert-butyldiphenylsilyl chloride or triisopropylsilyl chloride in a suitable solvent such as N,N-dimethylformamide, pyridine, dichloromethane, tetrahydrofuran or acetonitrile optionally in the presence of a suitable base such as imidazole, triethylamine, N,N-diisopropylethylamine, 4-(N,N-dimethylamino)pyridine or 2,6-lutidine, or by reacting compound (II) with a silyl triflate such as tert-butyldimethylsilyl trifluoromethanesulfonate in a suitable solvent such as dichloromethane optionally in the presence of a suitable base such as triethylamine.

Compound (III) wherein $R_1$ is alkylcarbonyl or alkenylcarbonyl such as acetyl, chloroacetyl or phenoxyacetyl or angeloyl and $R_2$ is hydrogen or alkylcarbonyl or alkenylcarbonyl, can for example be synthesised by reacting compound (II) with the corresponding acid chloride such as acetyl chloride, chloroacetyl chloride or phenoxyacetyl chloride or angeloyl chloride or by reacting compound (II) with an acid anhydride such as acetic anhydride, chloroacetic anhydride or phenoxyacetic anhydride or angelic acid anhydride in a suitable solvent such as pyridine or dichloromethane optionally in the presence of a suitable base such as N,N-diisopropylethylamine or 4-(N,N-dimethylamino)pyridine, or by reacting compound (II) with an acyl donor such as vinyl acetate or chloroacetic anhydride or vinyl angelate optionally in the presence of an enzyme as catalyst.

Compound (III) wherein $R_1$ is alkoxycarbonyl such as methoxycarbonyl or 9-fluorenylmethoxy carbonyl and $R_2$ is hydrogen or alkoxycarbonyl such as methoxycarbonyl or 9-fluorenylmethoxy carbonyl, can for example be synthesised by reacting compound (II) with the corresponding alkylchloro formate in a suitable solvent such as pyridine or dichloromethane optionally in the presence of a suitable base such as triethylamine or N,N,N',N'-tetramethylenediamine.

Compound (III) wherein $R_1$ is an arylsulfenyl such as 2,4-dinitrophenylsulfenyl and $R_2$ is hydrogen or an arylsulfenyl such as 2,4-dinitrophenylsulfenyl can for example be synthesised by reacting compound (II) with an optionally substituted sulfenylchloride such as as 2,4-dinitrophenylsulfenyl chloride in a suitable solvent such as dichloromethane optionally in the presence of a suitable base such as pyridine.

Compound (IV) wherein D represents an acetal such as benzylidene acetal can for example be synthesised by reacting compound (II) with an aldehyde such benzaldehyde or a dimethoxy acetal such as benzaldehyde dimethyl acetal in a suitable solvent such as dichloromethane or N,N-dimethylformamide or THF in the presence of a suitable acid such as p-toluenesulfonic acid; or a benzylidene acetal can for example be prepared by reacting compound (II) with an α,α-di-halo-toluene derivative such as for example α,α-dibromo-toluene or α,α-(bispyridinium)toluenedibromide in a suitable solvent such as pyridine, DMF or THF in the presence of a suitable base such as $K_2CO_3$ or LiHMDS.

Compound (IV) wherein D represents a ketal such as isopropylidene ketal can for example be synthesised by reacting compound (II) with a ketone such as acetone or a dimethoxy ketal such as 2,2-dimethoxy propane in a suitable solvent such as dichloromethane or N,N-dimethylformamide or THF in the presence of a suitable acid such as p-toluenesulfonic acid or methanesulfonic acid. Acetone and 2,2-dimethoxy propane can also act as solvents.

Compound (IV) wherein D represents a bis-acetal such as butane 2,3-bisacetal or cyclohexane-1,2-diacetal or a dispiroketals such as octahydro-[2,2']-bipyranyl ketal can be prepared by reacting compound (II) with 2,2,3,3-tetramethoxybutane or cyclohexane-1,2-dione and trimethyl orthoformate in the presence of a suitable acid such as p-toluenesulfonic acid in a suitable solvent such as methanol or by reacting with bisdihydropyran in the presence of a suitable acid such as p-toluenesulfonic acid in a suitable solvent such as dichloromethane.

Compound (IV) wherein D represents a cyclic ortho ester such as methoxymethylene acetal or 2-oxacyclopentylidene ortho ester can for example be synthesised by reacting compound II with an ortho ester such as trimethyl orthoformate in a suitable solvent such as dichloromethane in the presence of an acid such as p-toluenesulfonic acid; or by reacting compound II with a dihalomethylalkoxyether, such as for example dichloromethyl methyl ether, in a suitable solvent such as DMF or THF in the presence of a suitable base such as LiHMDS or $K_2CO_3$.

Compound (IV) wherein D represents silyl such as di-tert-butylsilylene can for example be synthesised by reacting compound II with a dialkylsilyl dichloride or a dialkylsilyl ditriflate such as di-tert-butylsilyl ditriflate in a solvent such as acetonitrile, dichloromethane or N,N-dimethylformamide optionally in the presence of a base such as triethylamine or 2,6-lutidine.

Compound (IV) wherein D represents carbonyl can for example be synthesised by reacting compound (II) with phosgene or N,N'-carbonyldiimidazole in pyridine.

Compound (IV) wherein D represents a boronate such as phenyl boronate can for example be synthesised by reacting compound (II) with phenylboronic acid in pyridine.

The synthesis of compounds of general formula (III) and (IV) from compound (II) may be performed both in a batch reactor and in a flow reactor, such as for example an Alfa Laval ART® Plate Reactor 37

The reagents for introducing the hydroxyl protective groups R1, R2 or D may be solid phase supported reagents such as for example polymer bound 2-Chlorotrityl chloride, acetylpolystyrene resin or 4-(4-Hydroxyphenyl)butan-2-one-based resins.

The compounds of the general formula (III) and (IV) can be esterified in the 3-position to obtain the compounds of the general formula (V) and (VI) by reaction of compound (III) or (IV) with angelic acid in the presence of a coupling reagent or with activated angelic acid derivatives. Compound (II) can be esterified to obtain compounds of the general formula (VII) by reaction of compound (II) with angelic acid in the presence of a coupling reagent or with activated angelic acid derivatives. The compounds may be prepared according to, but not limited to, methods for esterification described in "Esterification" by J. Otera, Wiley-VCH, 2003, which is hereby incorporated by reference, and references cited therein.

For example compound (V), (VI) or (VII) can be synthesised by reacting compound (III), (IV) or (II) with an activated angelic acid derivative such as angeloyl halide such as angeloyl chloride. The esterification by reaction with angeloyl chloride can take place without an activator, or it can take place in the presence of a base such as pyridine or triethylamine, LiHMDS or DMAP, in a suitable solvent such as for example pyridine or THF. Examples of the synthesis of angelic acid esters using angeloyl chloride can for example be found in Beeby, P. J., Tetrahedron Lett., (1977), 38, 3379-3382.

Compound (V), (VI) or (VII) can for example be synthesised by reacting compound (III), (IV) or (II) with an activated angelic acid derivative such as angelic anhydride. The esterification by reaction with angelic anhydride can take place without a catalyst, or in the presence of an acidic catalyst using an acid such as perchloric acid or a Lewis acid such as scandium (III) triflate or bismuth (III) triflate, or in the presence of a base such as sodium hydrogencarbonate or triethylamine, LiHMDS, NaHMDS, KHMDS, pyridine, cesium carbonate or DMAP, in a suitable solvent such as for example THF, MeCN, pyridine or MTBE. Examples of the synthesis of angelic acid esters using angelic acid anhydride can for example be found in Hartmann, B. et. al.; Tetrahedron Lett., (1991), 32, 5077-5080 or in JP2008127287.

Compound (V), (VI) or (VII) can for example be synthesised by reacting compound (III), (IV) or (II) with an activated angelic acid derivative such as a mixed anhydride such as angeloyl trichlorobenzoyl anhydride, such as angeloyl 2,4,6-trichlorobenzoyl anhydride. The esterification by reaction with a mixed anhydride can take place without a catalyst, or in the presence of an acidic catalyst using an acid such as perchloric acid or a Lewis acid such as scandium (III) triflate or bismuth (III) triflate, or in the presence of a base such as sodium hydrogencarbonate or triethylamine, in a suitable solvent such as for example toluene. Examples of the synthesis of angelic acid esters using angeloyl trichlorobenzoyl anhydride can for example be found in Hartmann, B. et. al.; Tetrahedron Lett. (1991), 32, 5077-5080, or in Ball, B., Org. Lett., (2007), 9, 663-666.

Compound (V), (VI) or (VII) can for example be synthesised by reacting compound (III), (IV) or (II) with angelic acid in the presence of a coupling reagent. Angelic acid can be esterified in the presence of a coupling reagent such as a carbodiimide such as dicyclohexylcarbodiimide or EDCI (N-(3-Dimethylaminopropyl)-N'-ethylcarbodiimide hydrochloride) with or without catalysts such as 1-hydroxybenzotriazole. Examples of the synthesis of angelic acid esters using dicyclohexylcarbodiimide with or without catalysts can for example be found in Hoskins, W. M., J. Chem. Soc. Perkin Trans. 1, (1977), 538-544. Other coupling reagents for esterification can for example be 2-halo-1-alkylpyridinium salts such as 1-methyl-2-chloro-pyridinium iodide, or hydroxybenzotriazol derivatives such as HBTU (O-(benzotriazol-1-yl)-N,N,N',N'-tetramethyluroniumhexafluorophosphate), or HATU (N,N,N',N'-Tetramethyl-O-(7-azabenzotriazol-1-yl) uronium hexafluorophosphate), or triazine derivatives such as DMTMM (4-(4,6-dimethoxy-1,3,5-triazin-2-yl)-4-methylmorpholinium chloride. Suitable solvents can be methylene chloride, toluene, DMF or THF. Solid-supported coupling reagents can also be used in the esterification step [Nam, N.-H., Journal of Combinatorial Chemistry, (203), 5, 479-545, or "Esterification" by J. Otera, Wiley-VCH, 2003] which are hereby incorporated by reference.

Compound (V), (VI), (VII) or (I) can for example be synthesised by reacting compound (III), (IV) or (II) with an angeloyl donor such as angelic acid anhydride, angelic acid ester such as vinyl angelate, or angelic acid thioester in the presence of an enzyme such as a lipase or an esterase. Examples of esterification of an ingenol derivative catalysed by lipase can be found in Teng, R. W., *Fitoterapia*, (2009), 80, 233-236 which is hereby incorporated by reference The synthesis of compounds of general formula (V) and (VI) from compound of general formula (III) and (IV) may be performed both in a batch reactor and in a flow reactor.

The reagents for the synthesis of compounds of general formula (V) and (VI) from compound of general formula (III) and (IV) may be solid phase supported reagents.

Ingenol-3-angelate (I) can be synthesised by selective removal of the protective groups, $R_1$ and $R_2$ or D, from the compounds of the general structure V or VI, according to methods well known to a person skilled in the art for deprotection of hydroxyl or dihydroxyl protective groups, such as methods described in "Protective Groups in Organic Synthesis", $4^{th}$ ed. P. G. M. Wuts; T. W. Greene, John Wiley, 2007 or in P. J. Kocienski, "Protecting Groups", $3^{rd}$ ed. G. Thieme, 2003 which are hereby incorporated by reference and references cited therein.

Ingenol-3-angelate (I) can be synthesised by selective removal of the angeloyl groups from the 20-position or from the 5- and the 20-positions of the compound of the general structure (VII).

For example compound (I) can be synthesised from compound (V) wherein $R_1$ represents hydrogen or alkyl such as triphenylmethyl and $R_2$ represents hydrogen or triphenylmethyl by reacting compound (V) with a suitable acid such as formic acid or trifluoroacetic acid in a suitable solvent such as ether, methanol or dichloromethane.

Compound (I) can for example be synthesised from compound (V) wherein $R_1$ represents hydrogen or alkyl such as p-methoxybenzylmethyl or allyl and $R_2$ represents hydrogen or p-methoxybenzylmethyl or allyl by reacting compound (V) with 2,5-dichloro-5,6-dicyano-p-benzoequinone (DDQ) in dichloromethane. The allyl group can also be removed by isomerisation of the olefin to a vinyl ether by reaction with a transition metal catalyst such as Wilkinson's catalyst (Rhodium(I) tris(triphenylphosphine) chloride), followed by cleavage of the vinyl ether in the presence of water.

Compound (I) can for example be synthesised from compound (V) wherein $R_1$ represents hydrogen or alkoxyalkyl such as 2-methoxyethoxymethyl and $R_2$ represents hydrogen or alkoxyalkyl such as 2-methoxyethoxymethyl by cleaving the acetal moiety of $R_1$ and/or $R_2$, for example by acid catalysed cleavage with a Lewis acid such as zinc (II) bromide or titanium (IV) chloride in a suitable solvent such as dichloromethane.

Compound (I) can for example be synthesised from compound (V) wherein $R_1$ represents hydrogen or alkoxyalkyl such as 2-tetrahydropyranyl and $R_2$ represents hydrogen or alkoxyalkyl such as 2-tetrahydropyranyl by cleaving the acetal moiety of $R_1$ and/or $R_2$, for example by acid catalysed cleavage in the presence of a suitable acid such as p-toluenesulfonic acid in a suitable solvent such as methanol.

Compound (I) can for example be synthesised from compound (V) wherein $R_1$ represents hydrogen or silyl such as tert-butyldimethylsilyl and $R_2$ represents hydrogen or silyl such as tert-butyldimethylsilyl by reacting compound (V) with a suitable acid such as hydrogen chloride in a suitable solvent such as methanol or by reacting with a fluoride source such as tetra n-butylammonium fluoride or tetrafluorosilane in a suitable solvent such as tetrahydrofuran or acetonitrile.

Compound (I) can for example be synthesised from compound (V) wherein $R_1$ represents hydrogen or alkylcarbonyl such as acetyl or chloroacetyl and $R_2$ represents hydrogen or alkylcarbonyl such as acetyl or chloroacetyl by hydrolysing the ester moiety of $R_1$ and/or $R_2$ by enzymatic catalysis utilising an enzyme such as a lipase, or by hydrolysing the ester moiety of $R_1$ and/or $R_2$ in a suitable solvent such as methanol or water in the presence of a suitable base such as potassium carbonate or in the presence of a suitable acid such as hydrogen chloride.

Compound (I) can for example be synthesised from compound V wherein $R_1$ represents hydrogen or alkoxycarbonyl such as 9-fluorenylmethoxycarbonyl and $R_2$ represents hydrogen or alkoxycarbonyl such as 9-fluorenylmethoxycarbonyl by cleaving the carbonate moiety of $R_1$ and/or $R_2$ by cleavage in the presence of a suitable base such as triethylamine in a suitable solvent such as pyridine.

Compound (I) can for example be synthesised from compound (V) wherein $R_1$ represents hydrogen or 2,4-dinitrophenylsulfenyl and $R_2$ represents hydrogen or 2,4-dinitrophenylsulfenyl by cleavage of the sulfenate moiety of $R_1$ and/or $R_2$ with a nucleophile such as sodium cyanide in a suitable solvent such as methanol.

Compound (I) can for example be synthesised from compound (VI) wherein D represents an acetal such as benzylidene acetal by cleaving the acetal moiety in the presence of a suitable acid such as acetic acid, trifluoroacetic acid or p-toluenesulfonic acid in a suitable solvent such as water, dichloromethane or methanol.

Compound (I) can for example be synthesised from compound (VI) wherein D represents a ketal such as isopropylidene ketal by cleaving the ketal moiety in the presence of a suitable acid such as aqueous hydrogen chloride, acetic acid, trifluoroacetic acid, p-toluenesulfonic acid, solid supported p-toluenesulfonic acid, methanesulfonic acid, phosphoric acid or formic acid, in a suitable solvent such as methanol, THF or isopropanol.

Compound (I) can for example be synthesised from compound (VI) wherein D represents a cyclic ortho ester such as methoxymethylene acetal by cleaving the orthoester moiety in the presence of a suitable acid such as aqueous hydrogen chloride or acetic acid in a suitable solvent such as dioxan or water.

Compound (I) can for example be synthesised from compound (VI) wherein D represents silyl such as di-tert-butylsilylene by reacting compound (VI) with fluoride source such as tetra n-butylammonium fluoride or tetrafluorosilane in a suitable solvent such as tetrahydrofuran or acetonitrile.

Compound (I) can for example be synthesised from compound (VI) wherein D represents carbonyl by cleaving the carbonate moiety in the presence of a suitable base such as pyridine in a suitable solvent such as water or by enzymatic catalysed hydrolysis in the presence of an enzyme such as a lipase or an esterase.

Compound (I) can for example be synthesised from compound (VI) wherein D represents a boronate such as phenyl boronate by transesterification with a diol such as 1,3-propanediol.

The synthesis of compound (I) from compounds of general formula (V) and (VI) may be performed both in a batch reactor and in a flow reactor. The reagents for the synthesis of compound (I) from compound of general formula (V) and (VI) may be solid phase supported reagents.

Compound (I) can for example be synthesised from compound (VII) wherein $R_3$ represents angeloyl or hydrogen by enzymatic catalysed hydrolysis of the ester moiety in the 20-position or in the 5- and 20-positions in the presence of an enzyme such as a lipase or an esterase.

In a still further aspect, the present invention relates to a compound of general structure (V), wherein $R_1$ represents a hydroxyl protective group and $R_2$ represents hydrogen or a hydroxyl protective group, or a compound of general structure (VI), wherein D represents a dihydroxyl protective group, or a compound of general structure (VII), wherein $R_3$ represents hydrogen or angeloyl.

EXAMPLES

General

All the starting materials used are commercially available, unless otherwise described. For proton nuclear magnetic resonance ($^1$H NMR) spectra, chemical shift values (δ) (in ppm) are quoted relative to the internal standard tetramethylsilane (δ=0.00). The value of a multiplet, either defined doublet (d), triplet (t), quartet (q) or a range (m) is given. All organic solvents used were anhydrous, unless otherwise specified.

Flash chromatography was performed on silica gel. Appropriate mixtures of ethyl acetate, dichloromethane, methanol, petroleum ether (bp. 40-60° C.), and heptane were used as eluents unless otherwise noted.

ABBREVIATIONS

Bu$_3$N: Tributylamine
CDI: 1,1'-Carbonyldiimidazole
Cs$_2$CO$_3$: Cesium carbonate
DCC: N,N'-Dicyclohexylcarbodiimide
DIPEA: N,N-Diisopropylethylamine
DMAP: 4-(Dimethylamino)pyridine
EDCI: N-(3-Dimethylaminopropyl)-N'-ethylcarbodiimide hydrochloride
HATU: N,N,N',N'-Tetramethyl-O-(7-azabenzotriazol-1-yl) uranium hexafluorophosphate
HCl: Hydrochloric acid
HOAt: 3H-[1,2,3]-Triazolo[4,5-b]pyridin-3-ol
K$_2$CO$_3$: Potassium carbonate
KHMDS: Potassium hexamethyldisilazide
LiHMDS: Lithium hexamethyldisilazide
MSA: Methanesulfonic acid
NaHMDS: Sodium hexamethyldisilazide
TEA: Triethylamine
CDCl$_3$: Deuterochloroform
DCM: Dichloromethane
DMF: N,N-Dimethylformamide
IPA: 2-Propanol (isopropyl alcohol)
MeCN: Acetonitrile
MeTHF: 2-Methyltetrahydrofuran
MTBE: Methyl tert-butyl ether
PhMe: Toluene
TFA: Trifluoroacetic acid
THF: Tetrahydrofuran
I: Ingenol
I-3-Ang: Ingenol-3-angelate
I-3-Tig: Ingenol-3-tiglate
I-3,4-A: Ingenol-3,4-acetonide
I-5,20-A: Ingenol-5,20-acetonide
I-3,4:5,20-A: Ingenol-3,4:5,20-diacetonide
I-5,20-A-3-Ang: Ingenol-5,20-acetonide-3-angelate
I-5,20-A-3-Tig: Ingenol-5,20-acetonide-3-tiglate
I-3,4-X: Ingenol-3,4-acetal/ketal
I-5,20-X: Ingenol-5,20-acetal/ketal
I-3,4:5,20-X: Ingenol-3,4:5,20-diacetal/diketal
AngOH: Angelic acid
Ang$_2$O: Angelic anhydride
AngOMe: Methyl angelate
AngCl: Angeloyl chloride
AngIm: Angeloyl imidazolide
AngOAt: Angeloyl HOAt ester
AngOTig: Angeloyl tiglate
TigOH: Tiglic acid
Tig$_2$O: Tiglic anhydride
TigOMe: Methyl tiglate
TigCl: Tigloyl chloride
$^1$H NMR: Proton nuclear magnetic resonance
TLC: Thin layer chromatography
Equiv.: Equivalents
N/A: Not applicable

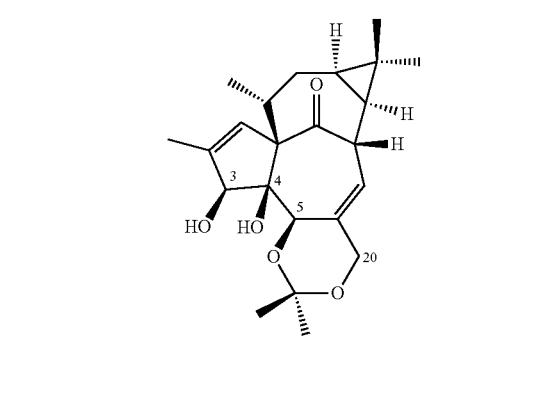

Preparation of ingenol-5,20-acetonide (Compound 1)

Example 1

Ingenol (1.00 g, 2.30 mmol) was dissolved in a solution of p-toluenesulphonic acid monohydrate in acetone (0.47 mg/mL, 22.5 mL). The solution was stirred at room temperature for 25 min. To this solution was added saturated aqueous solution of sodium hydrogencarbonate (0.2 mL). The obtained mixture was concentrated in vacuo. The residue was taken up in brine and extracted with ethyl acetate. The combined organic phases were dried over sodium sulfate and concentrated in vacuo. The residue was purified by flash chromatography (heptane/ethyl acetate 19:1→heptane/ethyl acetate 0:1), giving the title compound as a white solid (616 mg, 69%).

Also see: Opferkuch, H. J. et al., Z. Naturforsch. 1981, 36b, 878-887 (compound 4)

$^1$H NMR (300 MHz, CDCl$_3$) δ 5.91 (q, J=1.5 Hz, 1H), 5.82-5.77 (m, 1H), 4.25 (d, J=4.5 Hz, 1H), 4.20-4.07 (m, 3H), 3.93 (s, 1H), 3.51 (s, 1H), 2.57-2.41 (m, 2H), 2.25 (ddd, J=15.7, 8.4, 2.9 Hz, 1H), 1.85 (d, J=1.5 Hz, 3H), 1.77 (dt, J=15.8, 5.9 Hz, 1H), 1.41 (s, 3H), 1.35 (s, 3H), 1.13 (s, 3H), 1.05 (s, 3H), 1.00-0.87 (m, 4H), 0.70 (td, J=8.4, 6.4 Hz, 1H).

Example 2

Ingenol (7.0 g, 20.1 mmol) was dissolved in a solution of p-toluenesulfonic acid monohydrate in acetone (0.2 mg/mL, 200 mL). The solution was stirred at room temperature for 1.5 h (TLC control). To this solution was added saturated aqueous solution of sodium hydrogencarbonate (2.0 mL). The obtained mixture was filtered. The filtrate was concentrated in vacuo. The residue was taken up in ethyl acetate (20 mL). To this solution was added petroleum ether (40 mL). The mixture was let stand for 2 h. The crystals were filtered and dried, giving 4.5 g of the title compound. The mother liquor was purified by chromatography (petroleum ether/ethyl acetate 2:1 to 0:1), giving further 1.2 g of the title compound and 0.6 g of unreacted ingenol. The total yield was 73%, or 81% based on recovered ingenol.

Example 3

Dry ingenol (15.00 g, 90%, 38.75 mmol) was dissolved in acetone (630 mL) with stirring, and the solution was heated to 45° C. A solution of methanesulfonic acid (0.745 g, 7.75 mmol) in acetone (10 mL) was added during 5 seconds. The solution was stirred at 45° C. for an additional 95 seconds, before a solution of triethylamine (1.35 mL, 0.98 g, 9.69 mmol) in acetone (10 mL) was added during 5 seconds. The mixture was cooled to 20° C., and ethyl acetate (500 mL) was added. Most of the reaction solvent (650 mL) was distilled off under vacuum. Water (200 mL) was added to the remaining solution, and the mixture was agitated for 2 minutes. The water layer was removed, and the water wash was repeated once before the organic phase was concentrated under vacuum. The crude product contained 84% of the title compound as determined by $^1$H NMR spectroscopy. The residue was dissolved in toluene (75 mL) by heating to reflux temperature followed by slow cooling to 5° C. After 4 hours standing, the formed crystals were filtered off, rinsed with 5° C. toluene (2×5 mL) and dried under vacuum at 20° C. until constant weight. After 18 hours, ingenol-5,20-acetonide (8.97 g) was obtained.

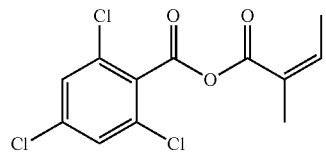 [SMILES: C/C=C(/C)C(=O)OC(=O)c1c(Cl)cc(Cl)cc1Cl]

Example 4

Preparation of [(Z)-2-methylbut-2-enoyl]2,4,6-trichlorobenzoate

Angelic acid (601 mg, 6.0 mmol) was dissolved in dichloromethane (3.0 mL) under argon. Diisopropylethylamine (1.23 mL, 7.20 mmol) was added at 5-10° C. in a period of 1 min. To this solution was added 2,4,6-trichlorobenzoyl chloride (1.12 mL, 7.20 mmol) at 3-6° C. in a period of 4 min. After the reaction solution had been stirred at 2° C. for 45 min, petroleum ether (9.0 mL) was added. The obtained suspension was purified by flash chromatography (petroleum ether/dichloromethane 3:1), giving the title compound as a white solid (605 mg, 33%).

$^1$H NMR (300 MHz, CDCl$_3$) δ 7.40 (s, 2H), 6.42 (qq, J=7.4, 1.5 Hz, 1H), 2.09 (dq, J=7.4, 1.5 Hz, 3H), 1.97 (p, J=1.5 Hz, 3H ($^1$H NMR data: see also Matthew, B et al.; *Org Lett*. 2007, 9, 663-666).

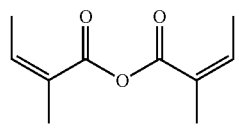

Example 5

Preparation of Angelic Anhydride

To a solution of angelic acid (5 g, 50 mmol) in dichloromethane (100 mL) was added N,N'-dicyclohexylcarbodiimide (8.6 mL, 60% in xylene, 25 mmol) at room temperature. The reaction mixture was stirred at this temperature for 1 h. The precipitate was filtered off. The filtrate was concentrated in vacuo. The residue was purified by chromatography (petroleum ether/ethyl acetate 10:1), giving 4.3 g of the title compound as an oil (94%).

$^1$H NMR (300 MHz, CDCl$_3$) δ 6.37-6.25 (m, 2H), 2.06 (dq, J=7.4, 1.5 Hz, 6H), 1.97-1.93 (m, 6H).

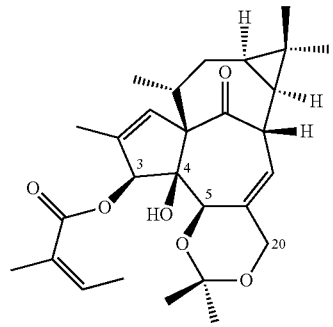

Preparation of ingenol-5,20-acetonide-3-angelate (compound 2)

Example 6

A mixture of ingenol-5,20-acetonide (233 mg, 0.60 mmol), [(Z)-2-methylbut-2-enoyl]2,4,6-trichlorobenzoate (231 mg, 0.75 mmol), and sodium hydrogencarbonate* (75.6 mg, 0.90 mmol) in toluene (2.5 mL) was stirred at 100° C. for 22 h. The mixture was then filtered and washed with toluene. The filtrate was concentrated in vacuo. The residue was purified by flash chromatography (heptane/ethyl acetate 19:1→heptane/ethyl acetate 3:2), giving the title compound as a white solid (215 mg, 76% yield).

* In the absence of sodium hydrogencarbonate, the product obtained contained 2-3% of ingenol-5,20-acetonide-3-tiglate.

$^1$H NMR (300 MHz, CDCl$_3$) δ 6.13-6.03 (m, 2H), 5.81-5.75 (m, 1H), 5.66 (s, 1H), 4.27-4.08 (m, 3H), 4.02 (s, 1H), 3.19 (s, 1H), 2.68-2.53 (m, 1H), 2.27 (ddd, J=15.8, 9.1, 3.0 Hz, 1H), 2.02-1.95 (m, 3H), 1.94-1.87 (m, 3H), 1.81-1.68 (m, 4H), 1.47 (s, 3H), 1.43 (s, 3H), 1.09 (s, 3H), 1.05 (s, 3H), 0.98 (d, J=7.1 Hz, 3H), 0.90 (dd, J=11.9, 8.4 Hz, 1H), 0.69 (td, J=8.7, 6.4 Hz, 1H).

Example 7

A mixture of ingenol-5,20-acetonide (1.32 g, 3.40 mmol), angelic anhydride (0.72 g, 3.94 mmol), and cesium carbonate (1.66 g, 5.10 mmol) in acetonitrile (26 mL) was stirred at room temperature for 2 h. The mixture was taken up in dichloromethane (30 mL) and washed with water. The aqueous phase was extracted three times with dichloromethane (3×4 mL). The combined organic phases were dried over sodium sulfate and concentrated in vacuo. The residue was purified by chromatography (petroleum ether/ethyl acetate 8:1), giving 1.46 g of the title compound (91%) as a white solid.

Example 8

Ingenol-5,20-acetonide (10.00 g, 25.74 mmol) was dissolved in tetrahydrofuran (100 mL) with stirring, and the solution was cooled to 10-15° C. A solution of lithium hexamethyldisilazide in tetrahydrofuran (1.0 M, 29.6 mL, 29.6 mmol) was added over a period of 10 minutes. Then a solution of angelic anhydride (5.51 mL, 5.62 g, 30.8 mmol) in tetrahydrofuran (70 mL) was added during 15 minutes. Ethyl acetate (200 mL) was added, and most of the reaction solvent (200 mL) was distilled off under vacuum. Water (75 mL) was added to the remaining solution, and the mixture was agitated for 2 minutes. The water layer was removed, and the water wash was repeated once before the organic phase was concentrated under vacuum. The residue was dissolved in methanol (61 mL) by heating to reflux temperature followed by slow cooling to 5° C. After 4 hours standing, the formed crystals were filtered off, rinsed with 5° C. methanol (2×5 mL) and dried under vacuum at 20° C. until constant weight. After 18 hours, ingenol-5,20-acetonide-3-angelate (8.78 g) was obtained.

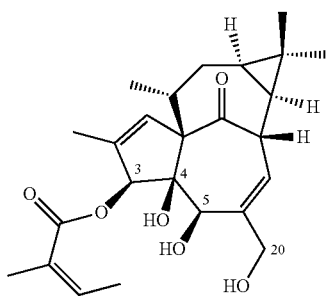

Preparation of Ingenol-3-Angelate (Compound 3)

Example 9

Ingenol-5,20-acetonide-3-angelate (7 mg, 0.015 mmol) in methanol, which contained 1% of concentrated aqueous hydrochloric acid solution, was stirred at room temperature for 1 h. The solution was diluted with ethyl ether. Water was added. After phase separation, the aqueous phase was extracted with ethyl ether. The combined organic phases were dried and concentrated in vacuo. The residue was purified by chromatography (petroleum ether/ethyl acetate 1:1), furnishing the product (4 mg, 63% yield).

$^1$H NMR (300 MHz, CDCl$_3$) δ 6.17 (qq, J=7.3, 1.4 Hz, 1H), 6.08-6.02 (m, 2H), 5.54 (s, 1H), 4.29 (d, J=4.5 Hz, 1H), 4.22-4.01 (m, 4H), 3.48 (s, 1H), 2.60-2.46 (m, 1H), 2.40-2.17 (m, 2H), 2.02 (dq, J=7.2, 1.4 Hz, 3H), 1.95-1.91 (m, 3H), 1.83-1.68 (m, 4H), 1.09 (s, 3H), 1.05 (s, 3H), 1.01-0.82 (m, 4H), 0.77-0.61 (m, 1H).

Example 10

A solution of ingenol-5,20-acetonide-3-angelate (1.46 g, 3.10 mmol) in methanol (30 mL), which contained 0.5% of concentrated aqueous hydrochloric acid solution, was stirred at room temperature for 1 h. The solution was then diluted with toluene and washed with water. The aqueous phase was extracted with ethyl ether. The combined organic phases were dried and concentrated in vacuo. The residue was purified by chromatography (petroleum ether/ethyl acetate 1:1 to 0:1), giving the product (1.20 g, 90%), which contained 2% of ingenol-3-tiglate.

Separation of ingenol angelate and ingenol tiglate by Preparative HPLC/MS:

Preparative HPLC/MS was performed on a Dionex APS-system with two PP150 preparative pumps and a Thermo MSQ Plus mass spectrometer.

Column: XTerra C-18, 150×19 mm, 5 µm;

Loading: 50 mg of ingenol angelate in 0.35 mL of acetonitrile;

Solvent system: eluent A: solution of 0.1% HCOOH in H$_2$O, eluent B: solution of 0.1% HCOOH in acetonitrile Flow rate: 18 mL/min; Run: 40% A/60% B; isocratic for 20 min.

The fractions were collected based on ion traces of relevant ions (MS-detector: MSQ from Dionex) and PDA signal (240-400 nm; detector: UVD 340 U from Dionex)

Example 11

Ingenol-5,20-acetonide-3-angelate (47.1 mg, 0.10 mmol) was dissolved in tetrahydrofuran (0.47 mL) under argon. An aqueous solution of hydrochloric acid (4 M, 4.7 µL) was added under ice-cooling. The solution was stirred at room temperature for 24 h. The solution was concentrated in vacuo. The residue was purified by flash chromatography (heptane/ethyl acetate 5:1 heptane/ethyl acetate 1:1), furnishing the title compound (30.8 mg, 72% yield) besides starting material (6.1 mg, 13%).

Example 12

Ingenol-5,20-acetonide-3-angelate (6.00 g, 12.75 mmol) was suspended in 2-propanol (152 mL) and stirred at 20° C. A solution of phosphoric acid (15.00 g, 153 mmol) in water (8 mL) was added, and the suspension was heated to 30-35° C. The resulting clear solution was stirred for 7 days. The reaction mixture was cooled to 20° C. and diluted with methyl tert-butyl ether (500 mL). Water (100 mL) was added, and the mixture was agitated for 2 minutes. The water layer was removed, and the water wash was repeated four times before the organic phase was concentrated under vacuum. Methyl tert-butyl ether (200 mL) was added followed by concentration. The crude product contained >95% ingenol-3-angelate. The residue was dissolved in acetonitrile (20 mL) by heating to reflux temperature. The solution was cooled to 5° C. After 24 hours standing at 5° C., the precipitated product was filtered off, rinsed with 5° C. acetonitrile (2×5 mL) and dried under vacuum at 20° C. until constant weight. After 18 hours, ingenol-3-angelate (3.91 g) was obtained.

Preparation of Compounds of General Formula (IV) from Ingenol

Example 13

Preparation of Symmetrical Ketals

The procedure described in Example 1 for the synthesis of ingenol-5,20-acetonide was used for the preparation of symmetrical ketals, replacing acetone with 3-pentanone, 2,4-dimethyl-3-pentanone, 2,6-dimethyl-4-heptanone, cyclopentanone or cyclohexanone, on a scale of 25-50 mg ingenol. Product Distribution is Shown in Table 1A
Products are Shown in Table 1B

TABLE 1A

| Synthesis of symmetrical ketals - acid catalyzed | |
|---|---|
| Reagent and solvent | Product distribution[a] |
| Propanone (acetone) | I-5,20-A (70-75%) |
| | I-3,4-A (5-10%) |
| | I-3,4:5,20-A (10-15%) |
| | I (5-10%) |
| 3-Pentanone | I-5,20-X (70-75%) |
| | I-3,4-X (5-10%) |
| | I-3,4:5,20-X (10-15%) |
| | I (5-10%) |
| 2,4-Dimethyl-3-pentanone | I-5,20-X (0-5%) |
| | I-3,4-X (0-5%) |
| | I-3,4:5,20-X (0-5%) |
| | I (90-95%) |
| 2,6-Dimethyl-4-heptanone | I-5,20-X (15-20%) |
| | I-3,4-X (15-20%) |
| | I-3,4:5,20-X (0-5%) |
| | I (60-65%) |
| Cyclopentanone | I-5,20-X (70-75%) |
| | I-3,4-X (5-10%) |
| | I-3,4:5,20-X (10-15%) |
| | I (5-10%) |
| Cyclohexanone | I-5,20-X (70-75%) |
| | I-3,4-X (5-10%) |
| | I-3,4:5,20-X (10-15%) |
| | I (5-10%) |

[a]The product distributions were estimated from $^1$H NMR and/or TLC data.

TABLE 1B

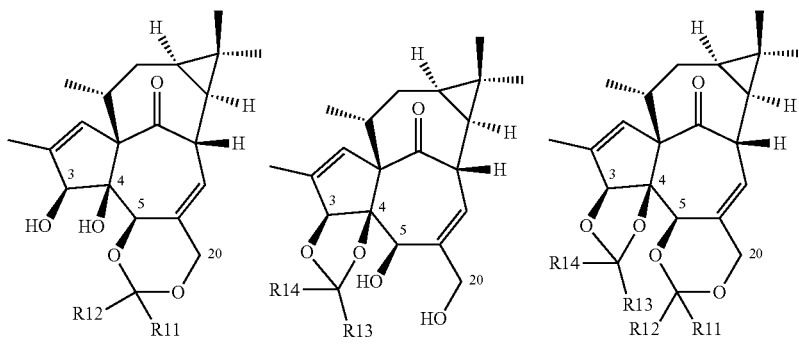

| Ingenol-5,20-ketal | Ingenol-3,4-ketal | Ingenol-3,4:5,20-diketal |
|---|---|---|
| $R^{11} = R^{12}$ = Methyl<br>Ingenol-5,20-acetonide | $R^{13} = R^{14}$ = Methyl<br>Ingenol-3,4-acetonide | $R^{11} = R^{12} = R^{13} = R^{14}$ = Methyl<br>Ingenol-3,4:5,20-diacetonide |
| $R^{11} = R^{12}$ = Ethyl<br>Ingenol-5,20-(3-pentylidene)-ketal<br>(Compound 4) | $R^{13} = R^{14}$ = Ethyl<br>Ingenol-3,4-(3-pentylidene)-ketal | $R^{11} = R^{12} = R^{13} = R^{14}$ = Ethyl<br>Ingenol-3,4:5,20-di[(3-pentylidene)-ketal] |
| $R^{11} = R^{12}$ = Prop-2-yl<br>Ingenol-5,20-(2,4-dimethyl-3-pentylidene)-ketal<br>(Compound 5) | $R^{13} = R^{14}$ = Prop-2-yl<br>Ingenol-3,4-(2,4-dimethyl-3-pentylidene)-ketal | $R^{11} = R^{12} = R^{13} = R^{14}$ = Prop-2-yl<br>Ingenol-3,4:5,20-di[(2,4-dimethyl-3-pentylidene)-ketal] |
| $R^{11} = R^{12}$ = 2-Methylprop-1-yl<br>Ingenol-5,20-(2,6-dimethyl-4-heptylidene)-ketal<br>(Compound 6) | $R^{13} = R^{14}$ = 2-Methylprop-1-yl<br>Ingenol-3,4-(2,6-dimethyl-4-heptylidene)-ketal | $R^{11} = R^{12} = R^{13} = R^{14}$ = 2-Methylprop-1-yl<br>Ingenol-3,4:5,20-di[(2,6-dimethyl-4-heptylidene)-ketal] |
| $R^{11}R^{12}$ = $CH_2CH_2CH_2CH_2$<br>Ingenol-5,20-cyclopentylidene-ketal<br>(Compound 7) | $R^{13}R^{14}$ = $CH_2CH_2CH_2CH_2$<br>Ingenol-3,4-cyclopentylidene-ketal | $R^{11}R^{12} = R^{13}R^{14}$ = $CH_2CH_2CH_2CH_2$<br>Ingenol-3,4:5,20-di(cyclopentylidene-ketal) |
| $R^{11}R^{12}$ = $CH_2CH_2CH_2CH_2CH_2$<br>Ingenol-5,20-cyclohexylidene-ketal<br>(Compound 8) | $R^{13}R^{14}$ = $CH_2CH_2CH_2CH_2CH_2$<br>Ingenol-3,4-cyclohexylidene-ketal | $R^{11}R^{12} = R^{13}R^{14}$ = $CH_2CH_2CH_2CH_2CH_2$<br>Ingenol-3,4:5,20-di(cyclohexylidene-ketal) |

Example 14

Preparation of Non-Symmetrical Ketals

The general procedure described in Example 15 was used for the preparation of non-symmetrical ketals, replacing the acetal/aldehyde with 3,3-dimethyl-2-butanone, acetophenone or (1,1-dimethoxyethyl)benzene, on a scale of 25-50 mg ingenol.

Product Distribution is Shown in Table 2A
Products are Shown in Table 2B

TABLE 2A

Synthesis of non-symmetrical ketals - acid catalyzed

| Reagent in THF | Product distribution[a] |
|---|---|
| 3,3-Dimethyl-2-butanone | I-5,20-X (20-30%) |
| | I-3,4-X (20-30%) |
| | I-3,4:5,20-X (10-20%) |
| | I (30-40%) |
| | Several other products observed by TLC |
| Acetophenone | No conversion |
| (1,1-Dimethoxyethyl)benzene | I-5,20-X (10-20%) |
| | I-3,4-X (30-40%) |
| | I-3,4:5,20-X (10-20%) |
| | I (30-40%) |
| | Several other products observed by TLC |

[a]The product distributions were estimated from $^1$H NMR and/or TLC data.

TABLE 2B

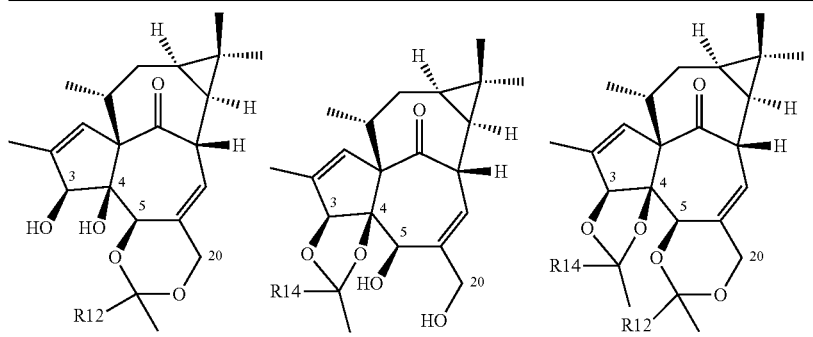

| Ingenol-5,20-ketal | Ingenol-3,4-ketal | Ingenol-3,4:5,20-diketal |
|---|---|---|
| $R^{12}$ = 1,1-Dimethylethyl Ingenol-5,20-(3,3-dimethyl-2-butylidene)-ketal (Compound 9) | $R^{14}$ = 1,1-Dimethylethyl Ingenol-3,4-(3,3-dimethyl-2-butylidene)-ketal | $R^{12}$ = $R^{14}$ = 1,1-Dimethylethyl Ingenol-3,4:5,20-di[(3,3-dimethyl-2-butylidene)-ketal] |
| $R^{12}$ = Phenyl Ingenol-5,20-(1-phenyl-1-ethylidene)-ketal (Compound 10) | $R^{14}$ = Phenyl Ingenol-3,4-(1-phenyl-1-ethylidene)-ketal | $R^{12}$ = $R^{14}$ = Phenyl Ingenol-3,4:5,20-di[(1-phenyl-1-ethylidene)-ketal] |

Example 15

General Procedure

Preparation of Acetals

Ingenol (25 mg, 72 μmol) was dissolved in tetrahydrofuran (622 μL) at 20° C. A solution of p-toluenesulfonic acid monohydrate in tetrahydrofuran (50 mg/mL, 0.26 M, 96 μL, 25 μmol) was added with stirring. The aldehyde/acetal (86 μmol) was added, and the progress of the reaction was monitored by TLC. The data provided were obtained after 21 hours of reaction time.

Product Distribution is Shown in Table 3A
Products are Shown in Table 3B

TABLE 3A

Synthesis of Acetals - acid catalyzed

| Reagent in THF | Product distribution[a] |
|---|---|
| Benzaldehyde | I-5,20-X (65-70%) (One epimer) |
| | I-3,4-X (5-10%) |
| | I-3,4:5,20-X (10-15%) |
| | I (10-15%) |
| | No epimers observed by TLC and $^1$H NMR |
| Benzaldehyde dimethylacetal | I-5,20-X (45-50%) (One epimer) |
| | I-3,4-X (5-10%) |
| | I-3,4:5,20-X (10-15%) |
| | I (30-35%) |
| | No epimers observed by TLC |
| | Several other products observed by TLC |
| 4-Methoxybenzaldehyde | I-5,20-X (10-20%) |
| | I-3,4-X (10-15%) |
| | I-3,4:5,20-X (5-10%) |
| | I (60-70%) |
| | No epimers observed by TLC |
| 2,4-Dimethoxybenzaldehyde | I-5,20-X (10-15%) |
| | I-3,4-X (5-10%) |
| | I-3,4:5,20-X (5-10%) |
| | I (70-75%) |
| | One other product observed by TLC |
| 4-Nitrobenzaldehyde | I-5,20-X (15-20%) |
| | I-3,4-X (5-10%) |

TABLE 3A-continued

Synthesis of Acetals - acid catalyzed

| Reagent in THF | Product distribution[a] |
|---|---|
| | I-3,4:5,20-X (5-10%) |
| | I (65-70%) |
| | No epimers observed by TLC |
| 2,4,6-Trimethylbenzaldehyde | I-5,20-X (15-20%) |
| | I-3,4-X (0-5%) |
| | I-3,4:5,20-X (10-15%) |

TABLE 3A-continued

Synthesis of Acetals - acid catalyzed

| Reagent in THF | Product distribution[a] |
|---|---|
| Trimethylacetaldehyde | I (65-70%)<br>No epimers observed by TLC<br>I-5,20-X (45-50%)<br>I-3,4-X (10-15%)<br>I-3,4:5,20-X (10-15%) |
|  | I (25-30%)<br>No epimers observed by TLC |

[a]The product distributions were estimated from $^1$H NMR and/or TLC data.

TABLE 3B

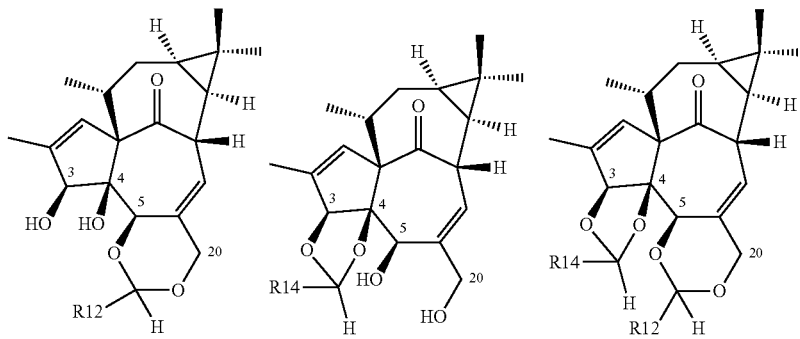

| Ingenol-5,20-acetal | Ingenol-3,4-acetal | Ingenol-3,4:5,20-diacetal |
|---|---|---|
| $R^{12}$ = Phenyl<br>Ingenol-5,20-benzylidene-acetal<br>(Compound 11) | $R^{14}$ = Phenyl<br>Ingenol-3,4-benzylidene-acetal | $R^{12} = R^{14}$ = Phenyl<br>Ingenol-3,4:5,20-di(benzylidene-acetal) |
| $R^{12}$ = 4-Methoxyphenyl<br>Ingenol-5,20-(4-methoxybenzylidene)-acetal<br>(Compound 12) | $R^{14}$ = 4-Methoxyphenyl<br>Ingenol-3,4-(4-methoxybenzylidene)-acetal | $R^{12} = R^{14}$ = 4-Methoxyphenyl<br>Ingenol-3,4:5,20-di[(4-methoxybenzylidene)-acetal] |
| $R^{12}$ = 2,4-Dimethoxyphenyl<br>Ingenol-5,20-(2,4-dimethoxybenzylidene)-acetal<br>(Compound 13) | $R^{14}$ = 2,4-Dimethoxyphenyl<br>Ingenol-3,4-(2,4-dimethoxybenzylidene)-acetal | $R^{12} = R^{14}$ = 2,4-Dimethoxyphenyl<br>Ingenol-3,4:5,20-di[(2,4-dimethoxybenzylidene)-acetal] |
| $R^{12}$ = 4-Nitrophenyl<br>Ingenol-5,20-(4-nitrobenzylidene)-acetal<br>(Compound 14) | $R^{14}$ = 4-Nitrophenyl<br>Ingenol-3,4-(4-nitrobenzylidene)-acetal | $R^{12} = R^{14}$ = 4-Nitrophenyl<br>Ingenol-3,4:5,20-di[(4-nitrobenzylidene)-acetal] |
| $R^{12}$ = 2,4,6-Trimethylphenyl<br>Ingenol-5,20-(2,4,6-trimethylbenzylidene)-acetal<br>(Compound 15) | $R^{14}$ = 2,4,6-Trimethylphenyl<br>Ingenol-3,4-(2,4,6-trimethylbenzylidene)-acetal | $R^{12} = R^{14}$ = 2,4,6-Trimethylphenyl<br>Ingenol-3,4:5,20-di[(2,4,6-trimethylbenzylidene)-acetal] |
| $R^{12}$ = 1,1-Dimethylethyl<br>Ingenol-5,20-(2,2-dimethyl-1-propylidene)-acetal<br>(Compound 16) | $R^{14}$ = 1,1-Dimethylethyl<br>Ingenol-3,4-(2,2-dimethyl-1-propylidene)-acetal | $R^{12} = R^{14}$ = 1,1-Dimethylethyl<br>Ingenol-3,4:5,20-di[(2,2-dimethyl-1-propylidene)-acetal] |

Example 16

General Procedure

Synthesis of Benzylidene Acetal

Ingenol (25 mg, 72 μmol) was dissolved in the solvent (622 μL) at 20° C. with stirring. For reactions conducted in pyridine, no further base was added. For reactions conducted in acetone or N,N-dimethylformamide, potassium carbonate (158 μmol) was added. For reactions conducted in tetrahydrofuran or 2-methyltetrahydrofuran, lithium hexamethyldisilazide (158 μmol) was added as a solution in tetrahydrofuran (1.0 M). A solution/suspension of the reagent (79 μmol) in the solvent (96 μL) was added dropwise. The progress of the reaction was monitored by TLC. For slow reactions, the temperature was increased from 20° C. to 50° C. and eventually to the boiling point of the solvent. The reaction of ingenol with α,α-dibromotoluene in pyridine was conducted at 100° C. for 3 hours. The reaction of ingenol with α,α-bis(pyridinium)toluene dibromide in tetrahydrofuran was conducted at 50° C. for 1 hour.

Product Distribution is Shown in Table 4A
Products are Shown in Table 4B

TABLE 4A

Synthesis of benzylidene acetal - base promoted

| Reagent | Solvent | Base | Product distribution[a] |
|---|---|---|---|
| α,α-Dichlorotoluene | Pyridine or acetone or DMF or MeTHF | $K_2CO_3$ (in acetone and DMF) or LiHMDS (in MeTHF) | No conversion |
| α,α-Dibromotoluene | Pyridine | Pyridine | I-5,20-X (85-90%) (One epimer) I-3,4-X (0-10%) I-3,4:5,20-X (0-10%) I (0-5%) |
| α,α-Bis(pyridinium)toluene dibromide[b] | THF | LiHMDS | I-5,20-X (20-30%) I-3,4-X (20-30%) I-3,4:5,20-X (20-30%) I (20-30%) Several other products observed by TLC |

TABLE 4A-continued

Synthesis of benzylidene acetal - base promoted

| Reagent | Solvent | Base | Product distribution[a] |
|---|---|---|---|
| α,α-Bis(4-(dimethylamino)pyridinium)-toluene dibromide[c] | Pyridine or DMF or THF | $K_2CO_3$ (in DMF) or LiHMDS (in THF) | No conversion |

[a]The product distributions were estimated from $^1$H NMR and/or TLC data.
[b]Preparation: cf. Acta Chem. Scand. 1972, 26, 3895-3901 and J. Org. Chem. 2007, 72, 9854-9856 (compound 1 in Scheme 2).
[c]Prepared by treatment of α,α-dibromotoluene (10 g, 0.04 mmol) with 4-(dimethylamino)pyridine (10.78 g, 0.088 mmol) in acetone (20 mL) at reflux for 1 hour.

Example 17

Synthesis of Orthoformates

The general procedure described in Example 15 was for the preparation of orthoformates, replacing the aldehyde/acetal with trimethyl orthoformate, triethyl orthoformate or tri(prop-2-yl) orthoformate, on a scale of 25-100 mg ingenol.

Product Distribution is Shown in Table 5A
Products are Shown in Table 5B

TABLE 5A

Synthesis of orthoformates - acid catalyzed

| Reagent in THF | Product distribution[a] |
|---|---|
| Trimethyl orthoformate | I-5,20-X (75-80%, 60:40 mixture of epimers) I-3,4-X (0-10%) I-3,4:5,20-X (0-10%) I (10-15%) |
| Triethyl orthoformate | I-5,20-X (75-80%, 60:40 mixture of epimers) I-3,4-X (0-10%) I-3,4:5,20-X (0-10%) I (10-15%) |
| Tri(prop-2-yl) orthoformate | I-5,20-X (75-80%, 60:40 mixture of epimers) I-3,4-X (0-10%) I-3,4:5,20-X (0-10%) I (10-15%) |

[a]The product distributions were estimated from $^1$H NMR and TLC data.

TABLE 5B

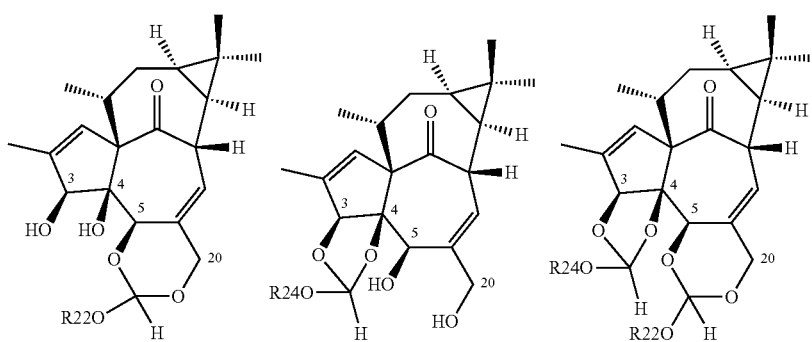

| Ingenol-5,20-orthoformate | Ingenol-3,4-orthoformate | Ingenol-3,4:5,20-diorthoformate |
|---|---|---|
| $R^{22}$ = Methyl Ingenol-5,20-methyl-orthoformate | $R^{24}$ = Methyl Ingenol-3,4-methyl-orthoformate | $R^{22} = R^{24}$ = Methyl Ingenol-3,4:5,20-di(methyl-orthoformate) |

TABLE 5B-continued

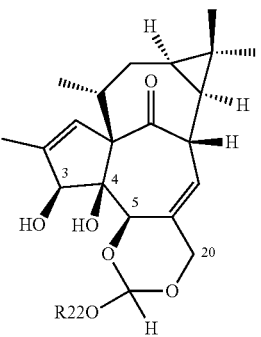

| Ingenol-5,20-orthoformate | Ingenol-3,4-orthoformate | Ingenol-3,4:5,20-diorthoformate |
|---|---|---|
| (Compound 17) $R^{22}$ = Ethyl Ingenol-5,20-ethyl-orthoformate (Compound 18) $R^{22}$ = Prop-2-yl Ingenol-5,20-(prop-2-yl)-orthoformate (Compound 19) | $R^{24}$ = Ethyl Ingenol-3,4-ethyl-orthoformate $R^{24}$ = Prop-2-yl Ingenol-3,4-(prop-2-yl)-orthoformate | $R^{22}$ = $R^{24}$ = Ethyl Ingenol-3,4:5,20-di(ethyl-orthoformate) $R^{22}$ = $R^{24}$ = Prop-2-yl Ingenol-3,4:5,20-di[(prop-2-yl)-orthoformate] |

Example 18

Synthesis of Methyl Orthoformate(Methoxymethylene Acetal)

The procedure described in Example 16 was employed using dichloromethyl methyl ether as the reagent, and using lithium hexamethyldisilazide in tetrahydrofuran. The reaction was conducted in tetrahydrofuran at 20° C. for 30 minutes.

TABLE 6A

Methyl orthoformate (methoxymethylene acetal) - base promoted

| Reagent | Solvent | Base | Product distribution[a] |
|---|---|---|---|
| Dichloromethyl methyl ether | THF | LiHMDS | I-5,20-X (10-15%) I-3,4-X (10-15%) I (50-60%) Several other products observed by TLC |

[a]The product distribution was estimated from TLC data.

Synthesis of Compounds of General Formula (VI)

Synthesis of Ingenol-5,20-Acetonide-3-Angelate Using Angelic Acid (AngOH)

Example 19A

General Procedure

Ingenol-5,20-acetonide (10.0 mg, 26 μmol) and angelic acid (2.6 mg, 26 μmol) were dissolved in the solvent (175 μL) at 20° C. with stirring. For reactions conducted in the presence of base, either 4-(dimethylamino)pyridine (6.3 mg, 52 μmol) or N,N-diisopropylethylamine (9 μL, 6.7 mg, 52 μmol) was added before the dropwise addition of a solution/suspension of the coupling reagent (26-52 μmol) in the solvent (75 μL). The progress of the reaction was monitored by TLC and $^1$H NMR spectroscopy.

Example 19B

Ingenol-5,20-acetonide (25.0 mg, 64 μmol), angelic acid (6.4 mg, 64 μmol) and 2-chloro-1-methyl-pyridinium iodide (19.7 mg, 77 μmol) (Mukaiyama's reagent) were suspended in toluene (108 μL). Tributylamine (37 μL, 29 mg, 155 μmol) was added, and the mixture was stirred at 60° C. for 18 hours. The progress of the reaction was monitored by TLC and $^1$H NMR spectroscopy.

Product Distribution and Reaction Conditions for Examples 19A and 19B are shown in table 7A
Products are Shown in Table 7B
The (E)/(Z) ratio is the Tiglate/Angelate ratio.

TABLE 7A

Synthesis of ingenol-5,20-acetonide-3-angelate using Angelic acid (AngOH)

| Reagent | Solvent | Products formed (crude yield)[a] | (E)/(Z)[b] |
|---|---|---|---|
| EDCI | CDCl$_3$ | Ang$_2$O | N/A |
| EDCI/DMAP | DCM | I-5,20-A-3-Tig (50-60%) and Ang$_2$O, AngOTig and Tig$_2$O | 96:4 |
| DCC | CDCl$_3$ | I-5,20-A-3-Ang (2%) and Ang$_2$O | 1:99 |
| DCC | PhMe | No conversion | N/A |
| DCC/DIPEA | PhMe | No conversion | N/A |
| DCC/DMAP | CDCl$_3$ | I-5,20-A-3-Tig (75%) | 85:15 |
| HATU/DIPEA | DMF | Initial formation of AngOAt (100%) Subsequent formal hydrolysis to AngOH and HOAt | N/A |
| 2-Chloro-1-methyl-pyridinium iodide/ Bu$_3$N | PhMe | I-5,20-A-3-Tig (30-40%) and Ang$_2$O, AngOTig and Tig$_2$O | 90:10 |

[a,b]The yields and (E)/(Z) ratios of were estimated from $^1$H NMR and TLC data.
[b](E)/(Z) ≥1:99 due to a content of 0.5-1% TigOH in AngOH.
The (E)/(Z) ratio is the I-5,20-A-3-Tig/I-5,20-A-3-Ang ratio

TABLE 7B

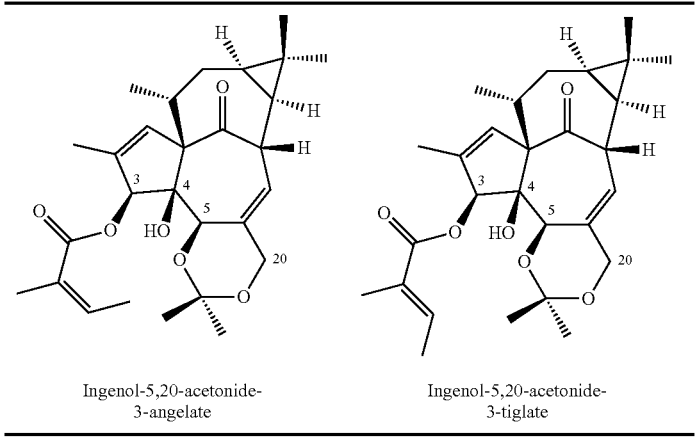

Ingenol-5,20-acetonide-3-angelate

Ingenol-5,20-acetonide-3-tiglate

Synthesis of ingenol-5,20-acetonide-3-angelate using Angelic anhydride

Example 20A

The procedure for the synthesis of ingenol-5,20-acetonide-3-angelate described in Example 8 was used for lithium hexamethyldisilazide in methyl tert-butyl ether, lithium hexamethyldisilazide in tetrahydrofuran, sodium hexamethyldisilazide in tetrahydrofuran and potassium hexamethyldisilazide in tetrahydrofuran on a scale of 25 mg-10 g ingenol-5,20-acetonide.

Example 20B

The experimental procedure for the synthesis of ingenol-5,20-acetonide-3-angelate using cesium carbonate is described in Example 7.

Example 20C

General Procedure

Ingenol-5,20-acetonide (15.0 mg, 39 μmol) was dissolved in pyridine (386 μL) or tetrahydrofuran (386 μL) at 20° C. with stirring. For the reaction conducted in pyridine, angelic anhydride (10.6 mg, 58 μmol) was added. For the reaction conducted in tetrahydrofuran, 4-(dimethylamino)pyridine (7.1 mg, 58 μmol) was added before the addition of angelic anhydride (10.6 mg, 58 μmol). The progress of the reaction was monitored by TLC and $^1$H NMR spectroscopy.

Product Distribution and Reaction Conditions for Examples 20A, 20B and 20C are shown in table 8A
Products are Shown in Table 7B
The (E)/(Z) ratio is the I-5,20-A-3-Tig/I-5,20-A-3-Ang-ratio.

TABLE 8

Synthesis of ingenol-5,20-acetonide-3-angelate using Angelic anhydride (Ang$_2$O)

| Reagent | Solvent | Products formed (crude yield)[a] | (E)/(Z)[b] |
|---|---|---|---|
| LiHMDS | MTBE | I-5,20-A-3-Ang (>95%) Slower conversion in MTBE than in THF due to low solubility | 2:98 |
| LiHMDS | THF | Rapid and clean conversion into I-5,20-A-3-Ang (>95%) | 2:98 |
| NaHMDS | THF | I-5,20-A-3-Ang (>95%) Slower conversion than with LiHMDS requiring larger excess of reagents | 2:98 |
| KHMDS | THF | I-5,20-A-3-Ang (>90%) Slower and less clean conversion than with LiHMDS and NaHMDS | 2:98 |
| Cs$_2$CO$_3$ | MeCN | I-5,20-A-3-Ang (>95%) | 2:98 |
| Pyridine | Pyridine | I-5,20-A-3-Tig (55%) | 96:4 |
| DMAP | THF | I-5,20-A-3-Tig (55%) | 96:4 |

[a,b]The yields and (E)/(Z) ratios were estimated from $^1$H NMR and TLC data.
[b](E)/(Z) ≥2:98 due to a content of 1.5-2% AngOTig in Ang$_2$O.
The (E)/(Z) ratio is the I-5,20-A-3-Tig/I-5,20-A-3-Ang ratio Synthesis of ingenol-5,20-acetonide-3-angelate using Angeloyl chloride

Example 21A

The procedure described in Example 8 for angelic anhydride was employed for the reaction between angeloyl chloride and ingenol-5,20-acetonide using lithium hexamethyldisilazide in tetrahydrofuran. The experiment was conducted on a scale of 25 mg ingenol-5,20-acetonide.

Example 21B

The procedure described in Example 20C for angelic anhydride was employed, replacing angelic anhydride with angeloyl chloride, for the reaction between angeloyl chloride and ingenol-5,20-acetonide in ethyl ether without base, in tetrahydrofuran without base, in pyridine and in tetrahydrofuran with 4-(dimethylamino)pyridine (1.5 equiv.) added. The experiments were conducted on a scale of 15-50 mg ingenol-5,20-acetonide.

Product Distribution and Reaction Conditions for Examples 21A and 21B are Shown in Table 9
Products are Shown in Table 7B
The (E)/(Z) ratio is the I-5,20-A-3-Tig/I-5,20-A-3-Ang ratio.

TABLE 9

Synthesis of ingenol-5,20-acetonide-3-angelate using Angeloyl chloride(AngCl)[c]

| Reagent | Solvent | Products formed (crude yield)[a] | (E)/(Z)[b] |
|---|---|---|---|
| LiHMDS | THF | I-5,20-A-3-Ang (60%) and I-5,20-A (30%) and other impurities (10%) | 3:97 |
| None | Ethyl ether | No conversion, low solubility | N/A |
| None | THF | No reaction | N/A |
| Pyridine | Pyridine | I-5,20-A-3-Tig (60-70%) and impurities (30%) | 96:4 |
| DMAP | THF | I-5,20-A-3-Tig (50-60%) | 96:4 |

[a,b]The yields and (E)/(Z) ratios were estimated from $^1$H NMR and TLC data.
[b](E)/(Z) ≥3:97 due to isomerization of AngCl to TigCl during storage.
The (E)/(Z) ratio is the I-5,20-A-3-Tig/I-5,20-A-3-Ang ratio
[c]Preparation: cf. Tetrahedron Letters 1977, 38, 3379-3382 (compound 2).

Synthesis of ingenol-5,20-acetonide-3-angelate using Methyl angelate

Example 22

The procedure described in Example 8 for angelic anhydride was employed for the reaction between methyl angelate and ingenol-5,20-acetonide using lithium hexamethyldisilazide in tetrahydrofuran. The experiment was conducted on a scale of 25 mg ingenol-5,20-acetonide.

TABLE 10

Synthesis of ingenol-5,20-acetonide-3-angelate using Methyl angelate (AngOMe)[c]

| Reagent | Solvent | Product formed (crude yield)[a] | (E)/(Z)[b] |
|---|---|---|---|
| LiHMDS | THF | I-5,20-A-3-Ang (7%) | 1:99 |

[a,b]The yield and (E)/(Z) ratio were estimated from $^1$H NMR and TLC data.
[b](E)/(Z) = 1:99 due to a content of 0.5-1% TigOMe in AngOMe.
The (E)/(Z) ratio is the I-5,20-A-3-Tig/I-5,20-A-3-Ang ratio
[c]Prepared by dropwise addition of a solution of (trimethylsilyl)diazomethane in ethyl ether (2.0M, 18.8 mL, 38 mmol) over a period of 175 minutes at 20° C. to a stirred solution of angelic acid (3.0 g, 30.0 mmol) in dichloromethane/methanol = 3:2 (30 mL). The reaction mixture was concentrated, and methyl angelate was purified by vacuum distillation. Also see J. Org. Chem. 1950, 15, 680-684.
$^1$H NMR (300 MHz, CDCl$_3$) δ 6.06 (qq, 1H), 3.74 (s, 3H), 1.98 (dq, 3H), 1.89 (quintet, 3H).

Example 23

General Procedure

Preparation of ingenol-3-angelate from ingenol-5,20-acetonide-3-angelate

Ingenol-5,20-acetonide-3-angelate (15 mg, 35 μmol) was dissolved/suspended in the organic solvent (331 μL) at 20° C. A solution of the catalyst in water (17 μL) was added with stirring resulting in a concentration of 0.1 M with respect to ingenol-5,20-acetonide-3-angelate. For formic acid/water (95:5), acetic acid/water (95:5) and trifluoroacetic acid/water (95:5), ingenol-5,20-acetonide-3-angelate was dissolved in the solvent mixture. The progress of the reaction was monitored by TLC and $^1$H NMR spectroscopy.
Product Distribution and Reaction Conditions for Examples 23 is Shown in Table 11A
Products are Shown in Table 11B

TABLE 11A

| Catalyst | pK$_a$ | Mol ratio[b] | Solvent | Temp °C. | (E)/(Z)[a] at complete conversion (days) | (E)/(Z)[a] after n days (days) | Comment |
|---|---|---|---|---|---|---|---|
| HCl | -8.0 | 1 | THF/H$_2$O 95:5 | 20 | 5:95 (4) | 19:81 (11) | Clean |
| HCl | -8.0 | 1 | MeOH/H$_2$O 95:5 | 20 | 3:97 (<1) | 6:94 (2) | Clean |
| HCl | -8.0 | 1 | IPA/H$_2$O 95:5 | 20 | 3:97 (3) | 14:86 (11) | Clean |
| MSA | -2.6 | 2 | THF/H$_2$O 95:5 | 20 | 2:98 (3) | 2:98 (4) | Clean |
| MSA | -2.6 | 2 | IPA/H$_2$O 95:5 | 20 | 2:98 (2) | 3:97 (10) | Clean |
| AG 50WX2 cation exch. resin | -2.6 | 2 | IPA/H$_2$O 95:5 | 20 | 2:98 (2) | 3:97 (13) | Clean |
| TFA | -0.25 | 6.5 | IPA/H$_2$O 95:5 | 20 | 3:97 (>4) | 3:97 (4) | Esterification[c] |
| TFA | -0.25 | 124 | TFA/H$_2$O 95:5 | 20 | N/A | N/A | Dec.[d] |
| H$_3$PO$_4$ | 2.12 | 12 | IPA/H$_2$O 95:5 | 30 | 2:98 (7) | 2:98 (10) | Clean |
| HCOOH | 3.77 | 252 | HCOOH/H$_2$O 95:5 | 20 | N/A | N/A | Dec.[d] |
| AcOH | 4.76 | 166 | AcOH/H$_2$O 95:5 | 20 | 2:98 (>4) | 2:98 (4) | Esterification[c] |

[a]The (E)/(Z) ratios were estimated by $^1$H NMR spectroscopy.
[a](E)/(Z) ≥ 2:98 due to a content of 1-2% I-5,20-A-3-Tig in I-5,20-A-3-Ang.
[b]Number of moles catalyst relative to I-5,20-A-3-Ang.
[c]Ester formation between catalyst and the ingenol 20-position.
[d]Decomposition.
The (E)/(Z) ratio is the I-3-Tig/I-3-Ang ratio

TABLE 11B

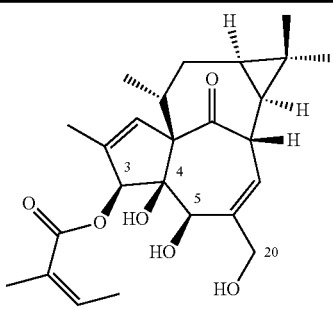

Ingenol-3-angelate

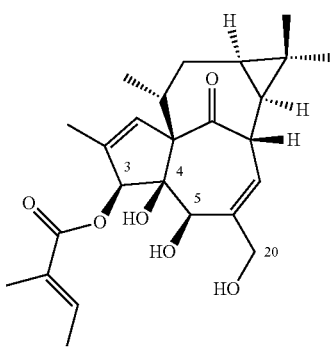

Ingenol-3-tiglate

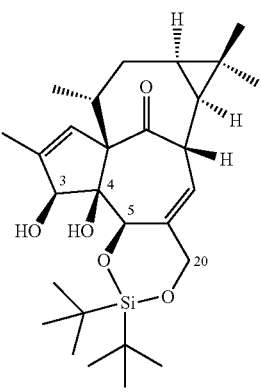

Example 24

Ingenol-5,20-(di(tert-butyl)silylene)-ether
(Compound 20)

To a solution of ingenol (50.4 mg, 0.145 mmol) and 2,6-lutidine (46.7 mg, 0.436 mmol) in N,N-dimethylformamide (0.25 mL) was added di(tert-butyl)silyl bis(trifluoromethanesulfonate) (76.6 mg, 0.174 mmol) at 0° C. The obtained solution was stirred at room temperature for 1 h. The reaction was quenched with saturated aqueous solution of sodium hydrogencarbonate. The mixture was then extracted twice with ethyl acetate. The combined organic phases were washed with saturated aqueous solution of sodium chloride, dried over sodium sulfate, and concentrated in vacuo. The residue was purified by flash chromatography (heptane/ethyl acetate 1:0→4:1), giving the title compound (35.7 mg, 50%) as a white foam.

$^1$H NMR (300 MHz, CDCl$_3$) δ 6.02 (d, J=5.1 Hz, 1H), 5.96 (q, J=1.5 Hz, 1H), 4.47 (d, J=12.5 Hz, 1H), 4.33-4.18 (m, 4H), 3.89 (s, 1H), 2.57-2.30 (m, 2H), 1.87 (d, J=1.5 Hz, 3H), 1.76 (ddd, J=15.8, 6.3, 3.9 Hz, 1H), 1.11 (s, 3H), 1.05 (s, 3H), 1.02-0.95 (m, 22H), 0.90 (dd, J=11.8, 8.4 Hz, 1H), 0.75-0.61 (m, 1H).

$C_{28}H_{44}O_5Si$

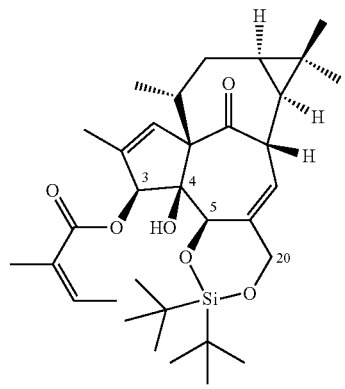

Example 25

Ingenol-5,20-(di(tert-butyl)silylene)-ether-3-angelate

Compound 21

A mixture of ingenol-5,20-(di(tert-butyl)silylene)-ether (35.5 mg, 0.073 mmol), [(Z)-2-methylbut-2-enoyl]2,4,6-trichlorobenzoate (29.7 mg, 0.097 mmol), and sodium hydrogencarbonate (10.2 mg, 0.12 mg) in toluene (0.3 mL) was stirred under argon atmosphere at 100° C. for 20 h. After being cooled to room temperature, the reaction mixture was filtered and washed with toluene. The filtrate was concentrated in vacuo. The residue was purified by flash chromatography (heptane/ethyl acetate 1:0→4:1), giving the title compound as a white foam (23.4 mg, 56%).

$^1$H NMR (300 MHz, CDCl$_3$) δ 6.10-5.96 (m, 3H), 5.67 (s, 1H), 4.49 (d, J=12.5 Hz, 1H), 4.35-4.21 (m, 3H), 3.64 (s, 1H), 2.64-2.52 (m, 1H), 2.46-2.27 (m, 1H), 2.01-1.93 (m, 3H), 1.91 (dq, J=3.0, 1.5 Hz, 3H), 1.82-1.65 (m, 4H), 1.10-1.04 (m, 15H), 1.03-0.95 (m, 12H), 0.94-0.84 (m, 1H), 0.67 (ddd, J=10.1, 8.4, 6.4 Hz, 1H).

$C_{33}H_{50}O_6Si$

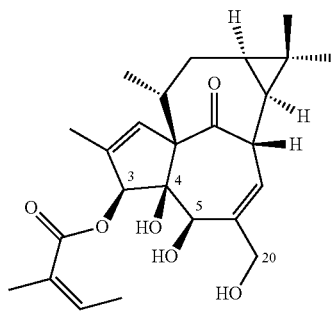

Example 26

Ingenol-3-angelate

To a solution of ingenol-5,20-(di(tert-butyl)silylene)-ether-3-angelate (10.3 mg, 0.018 mmol) in tetrahydrofuran (0.1 mL) was added tetrabutylammonium fluoride (1 M in tetrahydrofuran, 0.054 mmol) under argon atmosphere at −20° C. The solution was stirred at the same temperature for 15 min. The reaction was quenched with saturated aqueous solution of ammonium chloride. The mixture was extracted three times with ethyl acetate. The combined organic phases were dried over magnesium sulfate and concentrated. The residue was purified by chromatography (heptane/ethyl acetate 4:1-4:1), giving the title compound (2.2 mg, 29%).

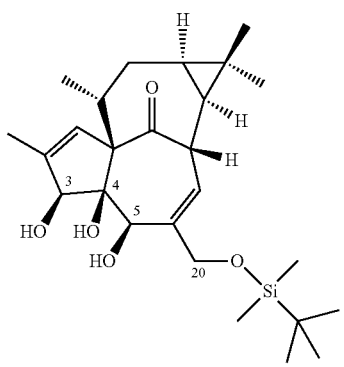

Example 27

Ingenol-20-(tert-butyldimethylsilyl)-ether (Compound 22)

To a solution of ingenol (66.2 mg, 0.15 mmol) and 2,6-lutidine (48.2 mg, 0.45 mmol) in N,N-dimethylformamide (0.25 mL) was added tert-butyldimethylsilyl chloride (27.1 mg, 0.18 mmol). The solution was stirred at the same temperature for 30 min. The reaction was not complete. 2,6-Lutidine (16.1 mg, 0.15 mmol) and tert-butyldimethylsilyl chloride (18.1 mg, 0.12 mmol) were added. The mixture was stirred at room temperature for 1 h, taken up in aqueous solution of sodium hydrogencarbonate, and extracted three times with ethyl acetate. The combined organic phases were dried over magnesium sulfate and concentrated in vacuo. The residue was purified by flash chromatography (heptane/ethyl acetate 3:1), providing an impure product. This impure product was subjected to a further chromatographic purification (dichloromethane/ethyl acetate 19:1-40:1), giving the title compound as a white foam (65.8 mg, 95%).

Also see: Opferkuch, H. J. et al., *Z. Naturforsch.* 1981, 36b, 878-887 (compound 10)

$^1$H NMR (300 MHz, CDCl$_3$) δ 6.11-5.94 (m, 1H), 5.96-5.84 (m, 1H), 4.44 (broad s, 1H), 4.32 (s, 1H), 4.29-4.07 (m, 3H), 4.01 (s, 1H), 3.86 (s, 1H), 2.57-2.39 (m, 1H), 2.32 (ddd, J=15.6, 9.1, 3.0 Hz, 1H), 1.85 (d, J=1.4 Hz, 3H), 1.75 (ddd, J=15.7, 6.2, 4.8 Hz, 1H), 1.11 (d, J=7.1 Hz, 3H), 1.06 (s, 3H), 0.96 (dd, J=7.6, 5.3 Hz, 3H), 0.89 (s, 9H), 0.88-0.80 (m, 1H), 0.78-0.60 (m, 1H), 0.08 (d, J=1.3 Hz, 6H).

$C_{36}H_{42}O_5Si$

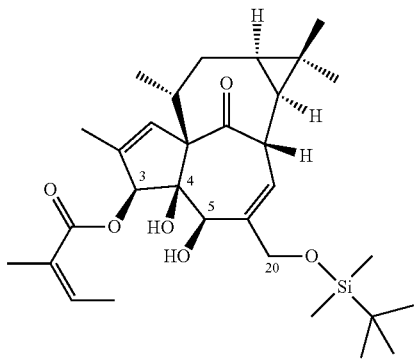

Example 28

Ingenol-20-(tert-butyldimethylsilyl)-ether-3-angelate

Compound 23

A mixture of ingenol-20-(tert-butyldimethylsilyl)-ether (61.6 mg, 0.133 mmol), [(Z)-2-methylbut-2-enoyl]2,4,6-trichlorobenzoate (54.4 mg, 0.177 mmol), and sodium hydrogencarbonate (16.8 mg, 0.20 mmol) in toluene (0.55 mL) was stirred under argon atmosphere at 100° C. for 17 h. After being cooled to room temperature, the reaction mixture was filtered and washed with toluene. The filtrate was concentrated in vacuo. The residue was purified by flash chromatography (heptane/ethyl acetate 89:1178:22), giving the title compound as a white foam (14.4 mg, 23%).

$^1$H NMR (300 MHz, CDCl$_3$) δ 6.08 (qd, J=7.2, 1.4 Hz, 1H), 6.03 (q, J=1.5 Hz, 1H), 5.96 (d, J=4.6 Hz, 1H), 5.69 (s, 1H), 4.76 (s, 1H), 4.29-4.07 (m, 3H), 4.01 (s, 1H), 3.65 (s, 1H), 2.69-2.51 (m, 1H), 2.33 (ddd, J=15.6, 9.6, 3.0 Hz, 1H), 2.03-1.95 (m, 3H), 1.97-1.85 (m, 3H), 1.82-1.65 (m, 4H), 1.07 (s, 3H), 1.03 (s, 3H), 0.96 (d, J=7.2 Hz, 3H), 0.93-0.80 (m, 10H), 0.67 (td, J=9.4, 6.4 Hz, 1H), 0.07 (s, 6H).

$C_{31}H_{48}O_6Si$

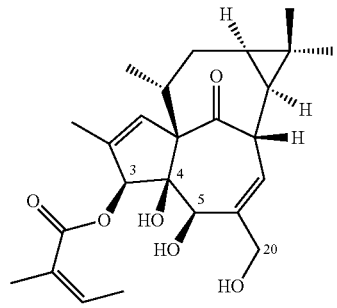

Example 29

Ingenol-3-angelate

Ingenol-20-(tert-butyldimethylsilyl)-ether-3-angelate (14.4 mg, 0.026 mmol) was dissolved in tetrahydrofuran (0.07 mL). To this solution was added hydrochloric acid in methanol (12.5 mM, 0.07 mL) at 0° C. The solution was stirred at room temperature for 6.5 h and then subjected to flash chromatography (heptane/ethyl acetate 2:1→4:1), giving the title compound (4.6 mg, 40%) and the starting material (4.4 mg).

The invention claimed is:
1. A method of producing ingenol-3-angelate (I) from ingenol (II):

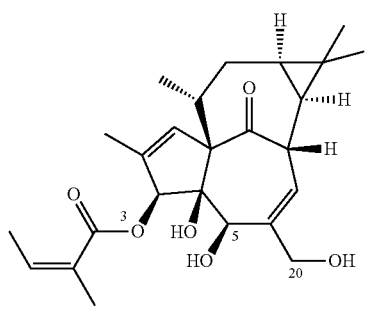
(I)

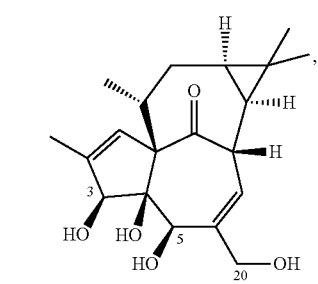
(II)

the method comprising the steps of:
(a) reacting one or both hydroxyl groups in positions 5 and 20 of ingenol (II) with suitable hydroxyl protecting agents, which may be the same or different, to obtain a compound of the general formula (III) or (IV)

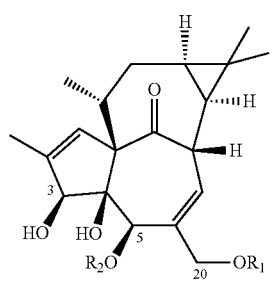
(III)

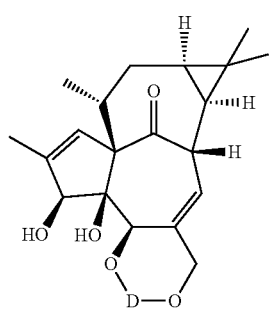
(IV)

wherein $R_1$ represents hydrogen or a hydroxyl protective group and $R_2$ represents hydrogen or a hydroxyl protective group, with the proviso that $R_1$ and $R_2$ are not both hydrogen, and wherein D represents a dihydroxyl protective group;
(b) esterifying the hydroxyl group at the 3-position of the compound of formula (III) or (IV) to obtain a compound of the general formula (V) or (VI)

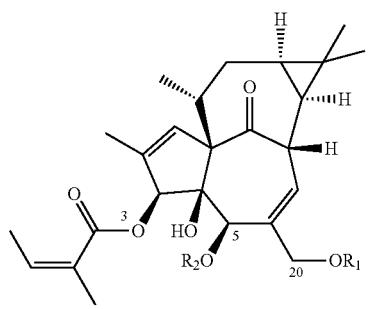
(V)

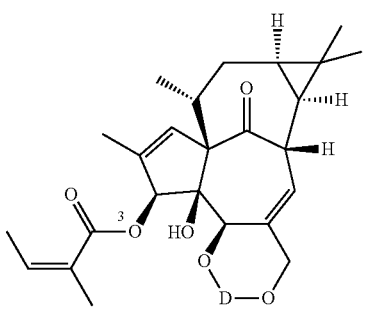
(VI)

wherein $R_1$, $R_2$ and D are as described above; and
(c) removing the hydroxyl protective groups $R_1$ or $R_2$, or $R_1$ and $R_2$, or D from the compound of formula (V) or (VI) to obtain ingenol-3-angelate (I).

2. A method of producing ingenol-3-angelate (I) from ingenol (II):

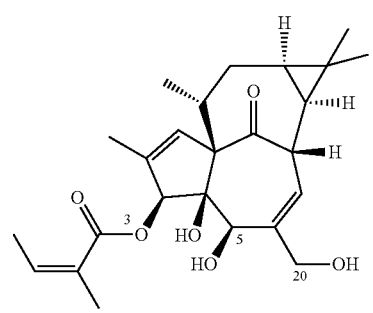
(I)

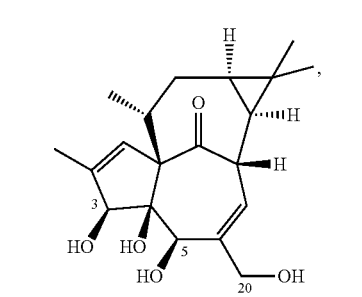
(II)

the method comprising the steps of:
(d) esterifying the 3- and the 20-hydroxyl group and optionally esterifying the 5-hydroxyl group of ingenol (II) to obtain a compound of the formula (VII)

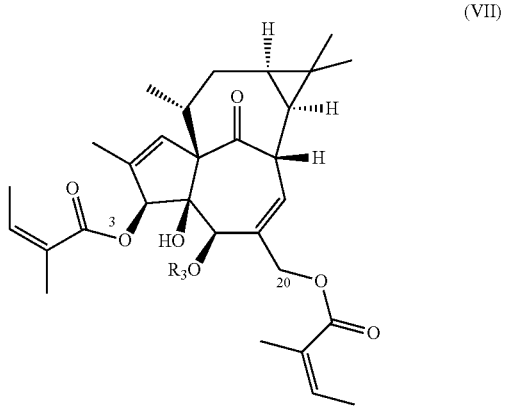

(VII)

wherein $R_3$ represents hydrogen or angeloyl; and
(e) cleaving the angelate ester(s) in position 20 or in position 5 and 20 of the compound of formula (VII) to obtain ingenol-3-angelate (I).

3. The method according to claim 1, wherein $R_1$ represents hydrogen or an ether, acetal, ketal, silylether, ester, carbonate, or a sulfenate derived hydroxyl protective group, and $R_2$ represents hydrogen or an ether, acetal, ketal, silylether, ester, carbonate, or a sulfenate derived hydroxyl protective group.

4. The method according to claim 1, wherein D represents an acetal, ketal, diacetal, diketal, ortho ester, silyl, boronate or a carbonate derived dihydroxyl protective group.

5. The method according to claim 1, wherein $R_1$ is selected from the group consisting of hydrogen or [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, acetyl, chloroacetyl, phenoxyacetyl or angeloyl.

6. The method according to claim 1, wherein $R_2$ is selected from the group consisting of hydrogen or [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, acetyl, chloroacetyl, phenoxyacetyl or angeloyl.

7. The method according to claim 1, wherein D is selected from the group consisting of isopropylidene, cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene, benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

8. The method according to claim 1, wherein $R_1$ represents a hydroxyl protective group and $R_2$ represents hydrogen.

9. The method according to claim 2, wherein $R_3$ represents hydrogen.

10. The method according to claim 1, wherein step (b) comprises reacting compound (III) or (IV) with angelic acid in the presence of a coupling reagent or an enzyme.

11. The method according to claim 1, wherein step (b) comprises reacting the compound of formula (III) or (IV) with angelic acid in the presence of a coupling reagent.

12. The method according to claim 1, wherein step (b) comprises reacting the compound of formula (III) or (IV) with angelic acid in the presence of N,N'-Dicyclohexylcarbodiimide, N,N,N',N'-Tetramethyl-O-(7-azabenzotriazol-1-yl)uronium hexafluorophosphate, N-(3-Dimethylaminopropyl)-N'-ethylcarbodiimide hydrochloride, N-(3-Dimethylaminopropyl)-N'-ethylcarbodiimide or 2-chloro-1-methyl-pyridinium iodide.

13. The method according to claim 1, wherein step (b) comprises reacting the compound of formula (III) or (IV) with an activated derivative of angelic acid.

14. The method according to claim 1, wherein step (b) comprises reacting the compound of formula (III) or (IV) with methyl angelate, angeloyl chloride, angelic acid anhydride, [(Z)-2-methylbut-2-enoyl]2,4,6-trichlorobenzoate, or angeloyl 4-nitrobenzoyl anhydride.

15. The method according to claim 1, wherein step (b) comprises reacting the compound of formula (III) or (IV) with an angelic acid halide or with angelic acid anhydride or with a mixed angelic acid anhydride.

16. The method according to claim 1, wherein step (b) comprises reacting the compound of formula (III) or (IV) with angeloyl chloride, angelic acid anhydride, [(Z)-2-methylbut-2-enoyl]2,4,6-trichlorobenzoate, or angeloyl 4-nitrobenzoyl anhydride.

17. A compound of general formula (V):

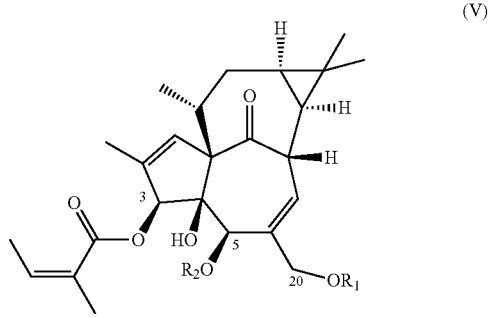

(V)

wherein $R_1$ represents hydrogen or a hydroxyl protective group and $R_2$ represents hydrogen or a hydroxyl protective group;
with the proviso that not both $R_1$ and $R_2$ represent hydrogen:
and with the proviso that $R_1$ and $R_2$ do not represent acetyl;
and with the proviso that $R_1$ and $R_2$ do not represent 2-[(2-aminobenzoyl)amino]benzoyl;
and with the proviso that $R_1$ does not represent decanoyl;
and with the proviso that $R_1$ does not represent 3-phenyl-2-propenoyl.

18. The compound according to claim 17, wherein $R_1$ represents hydrogen or an ether, acetal, ketal, silylether, ester, carbonate, or a sulfenate derived hydroxyl protective group, and $R_2$ represents hydrogen or an ether, acetal, ketal, silylether, ester, carbonate, or a sulfenate derived hydroxyl protective group.

19. The compound according to claim 17, wherein $R_1$ and $R_2$ independently represents hydrogen or [(3,4-dimethoxybenzyl)oxy]methyl, guaiacolmethyl, 2-methoxyethoxymethyl, tetrahydropyranyl, tetrahydrofuranyl, 1-ethoxyethyl, 1-methyl-1-methoxyethyl, allyl, prenyl, p-methoxybenzyl, triphenylmethyl, 2-(trimethylsilyl)ethoxymethyl, triethylsilyl, triisopropylsilyl, tert-butyldimethylsilyl, dimethylisopropylsilyl, diethylisopropylsilyl, tert-butyldiphenylsilyl, triphenylsilyl, chloroacetyl or phenoxyacetyl.

20. The compound according to claim 17, wherein $R_1$ represents a hydroxyl protective group and $R_2$ represents hydrogen.

21. The compound according to claim 17, wherein the compound is Ingenol-20-(tert-butyldimethylsilyl)-ether-3-angelate.

22. A compound of general formula (VI):

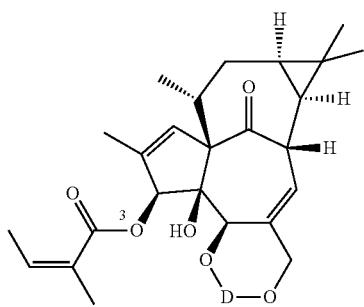

(VI)

wherein D represents a dihydroxyl protective group; with the proviso that D does not represent isopropylidene.

23. A compound according to claim 22, wherein D represents cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene,benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

24. The compound according to claim 22, wherein the compound is ingenol-5,20-(di(tert-butyl)silylene)-ether-3-angelate.

25. A compound of general formula (III):

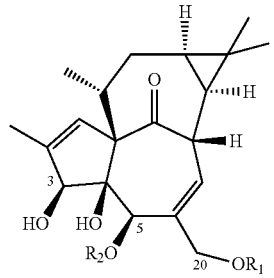

(III)

wherein $R_1$ and $R_2$ independently represents hydrogen or an ether, acetal, ketal, silylether, or a sulfenate derived hydroxyl protective group;
with the proviso that not both $R_1$ and $R_2$ represent hydrogen;
and with the proviso that $R_1$ does not represent triphenylmethyl;
and with the proviso that $R_1$ does not represent t-butyldimethylsilyl.

26. A compound of general formula IV:

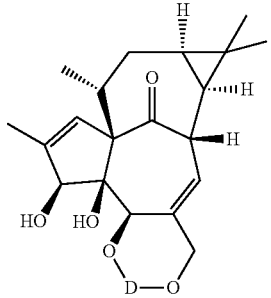

(IV)

wherein D represents cyclopentylidene, cyclohexylidene, p-methoxybenzylidene, methoxymethylene, 2-oxacyclopentylidene, 2,3-dimethoxybutane-2,3-di-yl, 1,2-dimethoxycyclohexan-1,2-di-yl, octahydro-[2,2']-bipyran-2,2'-di-yl, di-tert-butylsilylene, 1,3-(1,1,3,3-tetraisopropyldisiloxanylidene), phenyl boronate, 3-pentylidene, 2,4-dimethyl-3-pentylidene, 2,6-dimethyl-4-heptylidene, 3,3-dimethyl-2-butylidene, 1-phenyl-1-ethylidene,benzylidene, 2,4-dimethoxybenzylidene, 4-nitrobenzylidene, 2,4,6-trimethylbenzylidene, 2,2-dimethyl-1-propylidene, ethoxymethylene or isopropoxymethylene.

27. The compound according to claim 26, wherein the compound is selected from the group consisting of
Ingenol-5,20-(3-pentylidene)-ketal,
Ingenol-5,20-(2,4-dimethyl-3-pentylidene)-ketal,
Ingenol-5,20-(2,6-dimethyl-4-heptylidene)-ketal,
Ingenol-5,20-cyclopentylidene-ketal,
Ingenol-5,20-cyclohexylidene-ketal,
Ingenol-5,20-(3,3-dimethyl-2-butylidene)-ketal,
Ingenol-5,20-(1-phenyl-1-ethylidene)-ketal,
Ingenol-5,20-benzylidene-acetal,
Ingenol-5,20-(4-methoxybenzylidene)-acetal,
Ingenol-5,20-(2,4-dimethoxybenzylidene)-acetal,
Ingenol-5,20-(4-nitrobenzylidene)-acetal,
Ingenol-5,20-(2,4,6-trimethylbenzylidene)-acetal,
Ingenol-5,20-(2,2-dimethyl-1-propylidene)-acetal,
Ingenol-5,20-methyl-orthoformate,
Ingenol-5,20-ethyl-orthoformate,
Ingenol-5,20-(prop-2-yl)-orthoformate, and
Ingenol-5,20-(di(tert-butyl)silylene)-ether.

28. A compound of general structure (VII):

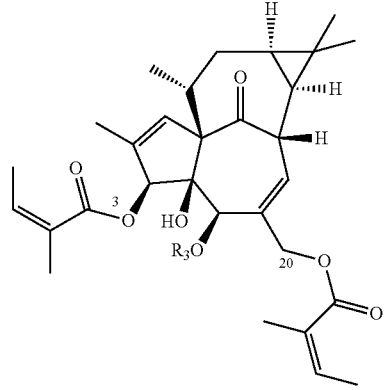

(VII)

wherein $R_3$ represents hydrogen or angeloyl.

* * * * *